(12) United States Patent
Nguyen et al.

(10) Patent No.: US 9,868,956 B2
(45) Date of Patent: Jan. 16, 2018

(54) METHODS

(75) Inventors: Duy P. Nguyen, Cambridge (GB);
Heinz Neumann, Gottingen (DE);
Alexander Deiters, Raleigh, NC (US);
Jason Chin, Cambridge (GB); Hrvoje Lusic, Raleigh, NC (US)

(73) Assignees: North Carolina State University, Raleigh, NC (US); Medical Research Council, Swindon (GB)

( * ) Notice: Subject to any disclaimer, the term of this patent is extended or adjusted under 35 U.S.C. 154(b) by 1194 days.

(21) Appl. No.: 13/376,068

(22) PCT Filed: Jun. 2, 2010

(86) PCT No.: PCT/GB2010/001083
§ 371 (c)(1),
(2), (4) Date: Dec. 2, 2011

(87) PCT Pub. No.: WO2010/139948
PCT Pub. Date: Dec. 9, 2010

(65) Prior Publication Data
US 2012/0077948 A1    Mar. 29, 2012

Related U.S. Application Data

(60) Provisional application No. 61/187,402, filed on Jun. 16, 2009.

(30) Foreign Application Priority Data

Jun. 4, 2009    (GB) .................................. 0909645.4

(51) Int. Cl.
*C12P 21/06* (2006.01)
*C12N 15/67* (2006.01)
(Continued)

(52) U.S. Cl.
CPC ............ *C12N 15/67* (2013.01); *C07C 233/49* (2013.01); *C07C 271/22* (2013.01); *C12N 9/93* (2013.01); *C12P 21/02* (2013.01)

(58) Field of Classification Search
CPC ........ C12N 15/67; C12N 9/93; C07C 233/49; C07C 271/22; C12P 21/02
See application file for complete search history.

(56) References Cited

FOREIGN PATENT DOCUMENTS

| EP | 1911840 | 4/2008 |
|---|---|---|
| WO | 2006/034332 | 3/2006 |

(Continued)

OTHER PUBLICATIONS

Xie et al., Adding amino acid to the genetic repertoire, Current Opinion in Chemical Biology 2005, 9:548-554.*

(Continued)

*Primary Examiner* — Reza Ghafoorian
(74) *Attorney, Agent, or Firm* — Thomas G. Peterson; Bradley Arant Boult Cummings LLP

(57) ABSTRACT

The invention relates to a method of making a polypeptide comprising an orthogonal functional group, said orthogonal functional group being comprised by an aliphatic amino acid or amino acid derivative, said method comprising providing a host cell; providing a nucleic acid encoding the polypeptide of interest; providing a tRNA-tRNA synthetase pair orthogonal to said host cell; adding an amino acid or amino acid derivative comprising the orthogonal functional group of interest, wherein said amino acid or amino acid derivative is a substrate for said orthogonal tRNA synthetase, wherein said amino acid or amino acid derivative has an aliphatic carbon backbone; and incubating to allow incorporation of said amino acid or amino acid derivative into the polypeptide of interest via the orthogonal tRNA-tRNA synthetase (Continued)

pair. The invention also relates to certain amino acids, and to polypeptides comprising same.

14 Claims, 7 Drawing Sheets

(51) Int. Cl.
*C07C 233/49* (2006.01)
*C07C 271/22* (2006.01)
*C12N 9/00* (2006.01)
*C12P 21/02* (2006.01)

(56) References Cited

FOREIGN PATENT DOCUMENTS

| WO | 2007/090198 | 8/2007 |
|----|-------------|--------|
| WO | 2008/134761 | 11/2008 |
| WO | 2009/056803 | 5/2009 |

OTHER PUBLICATIONS

Neumann et al., Genetically encoding N(epsilon)-acetyllysine in recombinant proteins, Nat Chem Biol. Apr. 2008;4(4):232-4.*
Mukai et al., Adding L-lysine derivatives to the genetic code of mammalian cells with engineered pyrrolysyl-tRNA synthetases, Biochemical and Biophysical Research Communications, vol. 371, Issue 4, Jul. 11, 2008, pp. 818-822.*
Yanagisawa et al, Multistep engineering of pyrrolysyl-tRNA synthetase to genetically encode N(epsilon)-(o-azidobenzyloxycarbonyl) lysine for site-specific protein modification, Chem Biol. Nov. 24, 2008;15(11):1187-97.*
Prescher et al., Chemistry in living systems, Nature Chemical Biology, vol. 1, No. 1, Jun. 13, 2005.*
Neumann et al., "Genetically encoding N•-acetyllsine in recombinant proteins," Nat. Chem. Biol., 4(4):232-234 (2008).
Takahito Mukai et al., "Adding •-lysine derivatives to the genetic code of mammalian cells with engineered pyrrolysyl-tRNA synthetases," Biochem. Biophys. Res. Commun., 371:818-822 (2008).
Tatsuo Yanagisawa et al., "Multistep Engineering of Pyrrolysyl-tRNA Synthetase to Genetically Encode N•-(o-Azidobenzyloxycarbonyl) lysine for Site-Specific Protein Modification," Chem. Biol., 15:1187-1197 (2008).
Ambrogelly et al., "Pyrrolysine is not hardwired for cotranslational insertion at UAG codons," Proc. Natl. Acad. Sci. USA, 104(9):3141-3146 (2007).
International Search Report in PCT/GB2010/001083, dated Mar. 28, 2011.
Kiick et al., "Incorporation of azides into recombinant proteins for chemoselective modification by the Staudinger ligation," Proc. Natl. Acad. Sci. USA, 99(1):19-24 (2002).
Polycarpo et al., "An aminoacyl-tRNA synthetase that specifically activates pyrrolysine," Proc. Natl. Acad. Sci. USA, 101(34):12450-12454 (2004).

* cited by examiner

STANDARD 1H OBSERVE

Pulse Sequence: s2pu1
  Solvent: D2O
  Ambient temperature
File: h1010709a-PrioTFAsaltlysine
Mercury-300BB "ncsumerc638"

Relax. delay 1.000 sec
Pulse 45.7 degrees
Acq. time 1.995 sec
Width 4506.5 Hz
16 repetitions
OBSERVE H1, 300.0961502 MHz
DATA PROCESSING
FT size 32768
Total time 0 min, 49 sec

Fig. 7 B

13C OBSERVE

Pulse Sequence: s2pul
  Solvent: D20
  Ambient temperature
File: h10108098-C13Prop-Lysine-Salt
Mercury-300BB
"ncsumerc638"

Relax. delay 4.000 sec
Pulse 40.3 degrees
Acq. time 1.815 sec
Width 18761.7 Hz
7408 repetitions
OBSERVE C13, 75.4592190 MHz
DECOUPLE H1, 300.0977099 MHz
  Power 30 dB
  continuously on
  WALTZ-16 modulated
DATA PROCESSING
Line broadening 1.0 Hz
FT size 131072
Total time 12 hr, 44 min, 2 sec

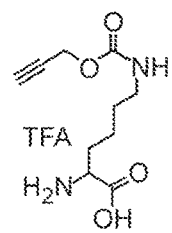

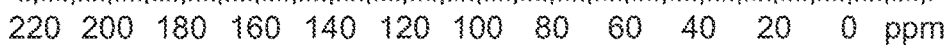
220 200 180 160 140 120 100 80 60 40 20 0 ppm

Fig. 7 C

STANDARD 1H OBSERVE

Pulse Sequence: s2pul
  Solvent: D20
  Ambient temperature
File: h1080208g-pentynoicamide-Lys-TFa
Mercury-300BB "ncsumerc638"

Relax. delay 1.000 sec
Pulse 45.7 degrees
Acq. time 1.995 sec
Width 4506.5 Hz
16 repetitions
OBSERVE H1, 300.0961502 MHz
DATA PROCESSING
FT size 32768
Total time 0 min, 49 sec

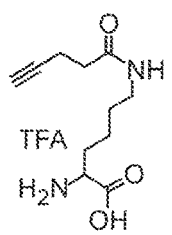

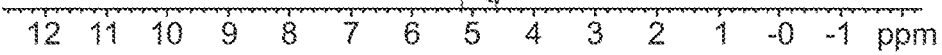
12 11 10 9 8 7 6 5 4 3 2 1 -0 -1 ppm

Fig. 7 D

13C OBSERVE
Pulse Sequence: s2pu1
 Solvent: D2O
 Ambient temperature
File: h1012509d-propamide-Lys-TFA
Mercury-300BB "ncsumerc638"

Relax. delay 2.000 sec
Pulse 40.3 degrees
Acq. time 1.815 sec
Width 18761.7 Hz
1024 repetitions
OBSERVE C13, 75.4592190 MHz
DECOUPLE H1, 300.0977099 MHz
 Power 30 dB
 continuously on
 WALTZ-16 modulated
DATA PROCESSING
Line broadening 1.0 Hz
FT size 131072
Total time 1 hr, 10 min, 10 sec

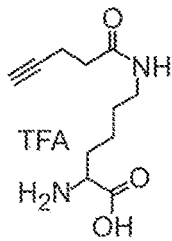

Fig. 7 E

STANDARD 1H OBSERVE
Pulse Sequence: s2pu1
 Solvent: D2O
 Ambient temperature
File: h1012509d-N3-Lys-TFA
Mercury-300BB "ncsumerc638"

Relax. delay 1.000 sec
Pulse 45.7 degrees
Acq. time 1.995 sec
Width 4506.5 Hz
16 repetitions
OBSERVE H1, 300.0961502 MHz
DATA PROCESSING
FT size 32768
Total time 0 min, 49 sec

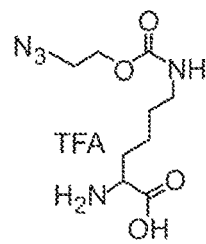
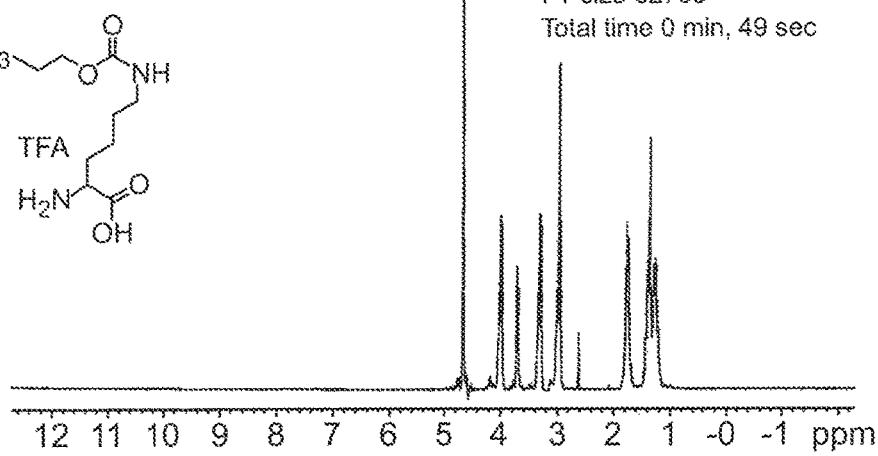

A

B

C

5

6

SEQUENCE LISTING

<160> NUMBER OF SEQ ID NOS: 13

<210> SEQ ID NO 1
<211> LENGTH: 419
<212> TYPE: PRT
<213> ORGANISM: Methanosarcina barkeri

<400> SEQUENCE: 1

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

```
Asp Arg Val Glu Ala Leu Leu Ser Pro Glu Asp Lys Ile Ser Leu Asn
            165                 170                 175

Met Ala Lys Pro Phe Arg Glu Leu Glu Pro Glu Leu Val Thr Arg Arg
        180                 185                 190

Lys Asn Asp Phe Gln Arg Leu Tyr Thr Asn Asp Arg Glu Asp Tyr Leu
    195                 200                 205

Gly Lys Leu Glu Arg Asp Ile Thr Lys Phe Phe Val Asp Arg Gly Phe
210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
            245                 250                 255

Asp Lys Asn Leu Cys Leu Arg Pro Met Leu Ala Pro Thr Leu Tyr Asn
        260                 265                 270

Tyr Leu Arg Lys Leu Asp Arg Ile Leu Pro Gly Pro Ile Lys Ile Phe
    275                 280                 285

Glu Val Gly Pro Cys Tyr Arg Lys Glu Ser Asp Gly Lys Glu His Leu
290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
            325                 330                 335

Ile Asp Phe Glu Ile Val Gly Asp Ser Cys Met Val Tyr Gly Asp Thr
        340                 345                 350

Leu Asp Ile Met His Gly Asp Leu Glu Leu Ser Ser Ala Val Val Gly
    355                 360                 365

Pro Val Ser Leu Asp Arg Glu Trp Gly Ile Asp Lys Pro Trp Ile Gly
370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
            405                 410                 415

Thr Asn Leu

<210> SEQ ID NO 2
<211> LENGTH: 1260
<212> TYPE: DNA
<213> ORGANISM: Methanosarcina barkeri

<400> SEQUENCE: 2
atggataaaa aaccgctgga tgtgctgatt agcgcgaccg gcctgtggat gagccgtacc      60
ggcaccctgc ataaaatcaa acatcatgaa gtgagccgca gcaaaatcta tattgaaatg     120
gcgtgcggcg atcatctggt ggtgaacaac agccgtagct gccgtaccgc gcgtgcgttt     180
cgtcatcata ataccgcaa aacctgcaaa cgttgccgtg tgagcgatga agatatcaac     240
aactttctga cccgtagcac cgaaagcaaa acagcgtgaa agtgcgtgt ggtgagcgcg     300 ccgaaagtga aaaagcgat gccgaaaagc gtgagccgtg cgccgaaacc gctggaaaat     360
agcgtgagcg cgaaagcgag caccaacacc agccgtagct tccgagcccc ggcgaaaagc     420
accccgaaca gcagcgttcc ggcgtctgcg ccggcaccga gcctgacccg cagccagctg     480
gatcgtgtgg aagcgctgct gtctccggaa gataaaatta gcctgaacat ggcgaaaccg     540
tttcgtgaac tggaaccgga actggtgacc cgtcgtaaaa acgattttca gcgcctgtat     600
```

```
accaacgatc gtgaagatta tctgggcaaa ctggaacgtg atatcaccaa atttttgtg      660 gatcgcggct ttctggaaat taaaagcccg attctgattc cggcggaata tgtggaacgt      720
atgggcatta caacgacac cgaactgagc aaacaaattt ccgcgtgga taaaaacctg       780 tgcctgcgtc cgatgctggc cccgaccctg tataactatc tgcgtaaact ggatcgtatt      840
ctgccgggtc cgatcaaaat tttgaagtg ggcccgtgct atcgcaaaga aagcgatggc       900
aaagaacacc tggaagaatt caccatggtt aactttgcc aaatgggcag cggctgcacc       960
cgtgaaaacc tggaagcgct gatcaaagaa ttcctggatt atctggaaat cgacttcgaa     1020
attgtgggcg atagctgcat ggtgtatggc gataccctgg atattatgca tggcgatctg     1080
gaactgagca gcgcggtggt gggtccggtt agcctggatc gtgaatgggg cattgataaa    1140
ccgtggattg cgcgggtt tggcctggaa cgtctgctga agtgatgca tggcttcaaa       1200 aacattaaac gtgcgagccg tagcgaaagc tactataacg gcattagcac gaacctgtaa    1260
```

<210> SEQ ID NO 3
<211> LENGTH: 72
<212> TYPE: DNA
<213> ORGANISM: Methanosarcina barkeri
<400> SEQUENCE: 3

```
gggaacctga tcatgtagat cgaatggact ctaaatccgt tcagccgggt tagattcccg       60
gggtttccgc ca                                                          72
```

<210> SEQ ID NO 4
<211> LENGTH: 419
<212> TYPE: PRT
<213> ORGANISM: Artificial Sequence
<220> FEATURE:
<223> OTHER INFORMATION: Methanosarcina barkeri mutant KtKRS-1

<400> SEQUENCE: 4

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190
```

Lys Asn Asp Phe Gln Arg Leu Tyr Thr Asn Asp Arg Glu Asp Tyr Leu
            195                 200                 205

Gly Lys Leu Glu Arg Asp Ile Thr Lys Phe Phe Val Asp Arg Gly Phe
        210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
            245                 250                 255

Asp Lys Asn Leu Cys Leu Arg Pro Met Leu Ala Pro Thr Leu Tyr Asn
            260                 265                 270

Tyr Gln Arg Lys Leu Asp Arg Ile Leu Pro Gly Pro Ile Lys Ile Phe
            275                 280                 285

Glu Val Gly Pro Cys Tyr Arg Lys Glu Ser Asp Gly Lys Glu His Leu
            290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
            325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
            355                 360                 365

Pro Val Ser Leu Asp Arg Glu Trp Gly Ile Asp Lys Pro Trp Ile Gly
            370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
            405                 410                 415

Thr Asn Leu

<210> SEQ ID NO 5
<211> LENGTH: 1260
<212> TYPE: DNA
<213> ORGANISM: Artificial Sequence
<220> FEATURE:
<223> OTHER INFORMATION: Methanosarcina barkeri mutant KtKRS-1

<400> SEQUENCE: 5
atggataaaa aaccgctgga tgtgctgatt agcgcgaccg gcctgtggat gagccgtacc      60
ggcaccctgc ataaaatcaa acatcatgaa gtgagccgca gcaaaatcta tattgaaatg     120
gcgtgcggcg atcatctggt ggtgaacaac agccgtagct gccgtaccgc gcgtgcgttt     180
cgtcatcata ataccgcaa acctgcaaa cgttgccgtg tgagcgatga agatatcaac      240
aactttctga cccgtagcac cgaaagcaaa acagcgtga agtgcgtgt ggtgagcgcg       300 ccgaaagtga aaaagcgat gccgaaaagc gtgagccgtg cgccgaaacc gctggaaaat     360
agcgtgagcg cgaaagcgag caccaacacc agccgtagcg ttccgagccc ggcgaaaagc     420
accccgaaca gcagcgttcc ggcgtctgcg ccggcaccga gcctgacccg cagccagctg     480
gatcgtgtgg aagcgctgct gtctccggaa gataaaatta gcctgaacat ggcgaaaccg     540
tttcgtgaac tggaaccgga actggtgacc cgtcgtaaaa acgattttca cgcctgtat     600 accaacgatc gtgaagatta tctgggcaaa ctgaacgtg atatcaccaa attttttgtg     660
gatcgcggct ttctggaaat taaaagcccg attctgattc cggcggaata tgtggaacgt     720

```
atgggcatta caacgacac cgaactgagc aaacaaattt tccgcgtgga taaaaacctg    780
tgcctgcgtc cgatgctggc gccgaccctg tataactatc agcgtaaact ggatcgtatt    840
ctgccgggtc cgatcaaaat ttttgaagtg ggcccgtgct atcgcaaaga aagcgatggc    900
aaagaacacc tggaagaatt caccatggtt aacttttgtc aaatgggcag cggctgcacc    960
cgtgaaaacc tggaagcgct gatcaaagaa ttcctggatt atctggaaat cgacttcgaa   1020
attgtgggcg atagctgcat ggtgtatggc gataccctgg atattatgca tggcgatctg   1080
gaactgagca gcgcggtggt gggtccggtt agcctggatc gtgaatgggg cattgataaa   1140
ccgtggattg gcgcgggttt tggcctggaa cgtctgctga agtgatgca tggcttcaaa   1200 aacattaaac gtgcgagccg tagcgaaagc tactataacg gcattagcac gaacctgtaa   1260
```

<210> SEQ ID NO 6
<211> LENGTH: 419
<212> TYPE: PRT
<213> ORGANISM: Artificial Sequence
<220> FEATURE:
<223> OTHER INFORMATION: Methanosarcina barkeri mutant KtKRS-2

<400> SEQUENCE: 6

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270
```

Tyr Asn Arg Lys Leu Asp Arg Ile Leu Pro Gly Pro Ile Lys Ile Phe
            275                 280                 285

Glu Val Gly Pro Cys Tyr Arg Lys Glu Ser Asp Gly Lys Glu His Leu
        290                 295                 300

Glu Glu Phe Thr Met Val Asn Phe Val Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 7
<211> LENGTH: 1260
<212> TYPE: DNA
<213> ORGANISM: Artificial Sequence
<220> FEATURE:
<223> OTHER INFORMATION: Methanosarcina barkeri mutant KtKRS-2

<400> SEQUENCE: 7

```
atggataaaa aaccgctgga tgtgctgatt agcgcgaccg gcctgtggat gagccgtacc      60
ggcaccctgc ataaaatcaa acatcatgaa gtgagccgca gcaaaatcta tattgaaatg     120
gcgtgcggcg atcatctggt ggtgaacaac agccgtagct gccgtaccgc gcgtgcgttt     180
cgtcatcata ataccgcaa acctgcaaa cgttgccgtg tgagcgatga agatatcaac      240
aactttctga cccgtagcac cgaaagcaaa acagcgtga agtgcgtgt ggtgagcgcg      300
ccgaaagtga aaaagcgat gccgaaaagc gtgagccgtc gccgaaacc gctggaaaat      360
agcgtgagcg cgaaagcgag caccaacacc agccgtagcg ttccgagccc ggcgaaaagc      420
accccgaaca gcagcgttcc ggcgtctgcg ccggcaccga gctgacccg cagccagctg      480
gatcgtgtgg aagcgctgct gtctccggaa gataaaatta gcctgaacat ggcgaaaccg      540
tttcgtgaac tggaaccgga actggtgacc gtcgtaaaa acgattttca gcgcctgtat      600
accaacgatc gtgaagatta tctgggcaaa ctggaacgtg atatcaccaa atttttgtg      660
gatcgcggct ttctggaaat taaaagcccg attctgattc cggcggaata tgtggaacgt      720
atgggcatta caacgacac cgaactgagc aaacaaattt tccgcgtgga taaaaacctg      780
tgcctgcgtc cgatgctggc gccgacccctg tataactata tcgtaaact ggatcgtatt      840
ctgccgggtc cgatcaaaat ttttgaggtg ggcccgtgct atcgcaaaga aagcgatggc      900
aaagaacacc tggaagaatt caccatggtt aactttgtgc aaatgggcag cggctgcacc      960
cgtgaaaacc tggaagcgct gatcaaagaa ttcctggatt atctggaaat cgacttcgaa     1020
attgtgggcg atagctgcat ggtgtatggc gatacccctg gatattatgca tggcgatctg     1080
gaactgagca gcgcggtggt gggtccggtt agcctggatc gtgaatgggg cattgataaa     1140
ccgtggattg gcgcgggttt tggcctggaa cgtctgctga aagtgatgca tggcttcaaa     1200
```
aacattaaac gtgcgagccg tagcgaaagc tactataacg gcattagcac gaacctgtaa    1260

<210> SEQ ID NO 8
<211> LENGTH: 419
<212> TYPE: PRT
<213> ORGANISM: Artificial Sequence
<220> FEATURE:
<223> OTHER INFORMATION: Methanosarcina barkeri mutant KtKRS-3

<400> SEQUENCE: 8

```
Met Asp Lys Lys Pro Leu Asp Val Leu Ile Ser Ala Thr Gly Leu Trp
 1               5                  10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Asn Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Val Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
```

355                 360                 365
Pro Val Ser Leu Asp Arg Glu Trp Gly Ile Asp Lys Pro Trp Ile Gly
            370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 9
<211> LENGTH: 1260
<212> TYPE: DNA
<213> ORGANISM: Artificial Sequence
<220> FEATURE:
<223> OTHER INFORMATION: Methanosarcina barkeri mutant KtKRS-3

<400> SEQUENCE: 9

```
atggataaaa aaccgctgga tgtgctgatt agcgcgaccg gcctgtggat gagccgtacc        60
ggcaccctgc ataaaatcaa acatcatgaa gtgagccgca gcaaaatcta tattgaaatg       120
gcgtgcggcg atcatctggt ggtgaacaac agccgtagct gccgtaccgc gcgtgcgttt       180
cgtcatcata ataccgcaa acctgcaaa cgttgccgtg tgagcgatga agatatcaac         240
aactttctga cccgtagcac cgaaagcaaa acagcgtga agtgcgtgt ggtgagcgcg         300 ccgaaagtga aaaagcgat gccgaaaagc gtgagccgtg cgccgaaacc gctggaaaat       360
agcgtgagcg cgaaagcgag caccaacacc agccgtagcg ttccgagccc ggcgaaaagc      420
accccgaaca gcagcgttcc ggcgtctgcg ccggcaccga gctgacccg cagccagctg       480 gatcgtgtgg aagcgctgct gtctccggaa gataaaatta gcctgaacat ggcgaaaccg      540
tttcgtgaac tggaaccgga actggtgacc cgtcgtaaaa acgattttca gcgcctgtat      600
accaacgatc gtgaagatta ctgggcaaa ctggaacgtg atatcaccaa attttttgtg       660
gatcgcggct ttctggaaat taaaagcccg attctgattc cggcggaata tgtggaacgt     720
atgggcatta caacgacac cgaactgagc aaacaaattt tccgcgtgga taaaaacctg      780
tgcctgcgtc cgatgctggc gccgaccctg tataactata tcgtaaact ggatcgtatt       840 ctgccgggtc cgatcaaaat tttttgaagtg ggcccgtgct atcgcaaaga aagcgatggc     900
aaagaacacc tggaagaatt caccatggtt aactttgttc aaatgggcag cggctgcacc      960 cgtgaaaaacc tggaagcgct gatcaaagaa ttcctggatt atctggaaat cgacttcgaa    1020
attgtgggcg atagctgcat ggtgtatggc gataccctgg atattatgca tggcgatctg    1080
gaactgagca gcgcggtggt gggtccggtt agcctggatc gtgaatgggg cattgataaa    1140
ccgtggattg gcgcgggttt tggcctggaa cgtctgctga aagtgatgca tggcttcaaa    1200
aacattaaac gtgcgagccg tagcgaaagc tactataacg gcattagcac gaacctgtaa    1260
```

<210> SEQ ID NO 10
<211> LENGTH: 419
<212> TYPE: PRT
<213> ORGANISM: Artificial Sequence
<220> FEATURE:
<223> OTHER INFORMATION: Methanosarcina barkeri mutant KtKRS-4

<400> SEQUENCE: 10

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser

```
            20                  25                  30
Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
        130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
        210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Met Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
        290                 295                 300

Glu Glu Phe Thr Met Val Asn Phe Ala Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
        370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 11
<211> LENGTH: 1260
```

```
<212> TYPE: DNA
<213> ORGANISM: Artificial Sequence
<220> FEATURE:
<223> OTHER INFORMATION: Methanosarcina barkeri mutant KtKRS-4

<400> SEQUENCE: 11
atggataaaa aaccgctgga tgtgctgatt agcgcgaccg gcctgtggat gagccgtacc      60
ggcaccctgc ataaaatcaa acatcatgaa gtgagccgca gcaaaatcta tattgaaatg     120
gcgtgcggcg atcatctggt ggtgaacaac agccgtagct gccgtaccgc gcgtgcgttt     180
cgtcatcata ataccgcaaa acctgcaaaa cgttgccgtg tgagcgatga agatatcaac     240
aactttctga cccgtagcac cgaaagcaaa aacagcgtga agtgcgtgt ggtgagcgcg      300
ccgaaagtga aaaagcgat gccgaaaagc gtgagccgtg cgccgaaacc gctggaaaat     360
agcgtgagcg cgaaagcgag caccaacacc agccgtagcg ttccgagccc ggcgaaaagc     420
accccgaaca gcagcgttcc ggcgtctgcg ccggcaccga gcctgacccg cagccagctg     480
gatcgtgtgg aagcgctgct gtctccggaa gataaaatta gcctgaacat ggcgaaaccg     540
tttcgtgaac tggaaccgga actggtgacc cgtcgtaaaa acgattttca gcgcctgtat     600
accaacgatc gtgaagatta tctgggcaaa ctggaacgtg atatcaccaa atttttgtg      660
gatcgcggct ttctggaaat taaaagcccg attctgattc cggcggaata tgtggaacgt     720
atgggcatta caacgacac cgaactgagc aaacaaattt tccgcgtgga taaaaacctg      780
tgcctgcgtc cgatgctggc tccgaccctg tataactata tgcgtaaact ggatcgtatt     840
ctgccgggtc cgatcaaaat ttttgaagtg ggcccgtgct atcgcaaaga aagcgatggc     900
aaagaacacc tggaagaatt caccatggtt aactttgctc aaatgggcag cggctgcacc     960
cgtgaaaacc tggaagcgct gatcaaagaa ttcctggatt atctggaaat cgacttcgaa    1020
attgtgggcg atagctgcat ggtgtatggc gataccctgg atattatgca tggcgatctg    1080
gaactgagca gcgcggtggt gggtccggtt agcctggatc gtgaatgggg cattgataaa    1140
ccgtggattg gcgcgggttt tggcctggaa cgtctgctga aagtgatgca tggcttcaaa    1200
aacattaaac gtgcgagccg tagcgaaagc tactataacg gcattagcac gaacctgtaa    1260

<210> SEQ ID NO 12
<211> LENGTH: 419
<212> TYPE: PRT
<213> ORGANISM: Artificial Sequence
<220> FEATURE:
<223> OTHER INFORMATION: Methanosarcina barkeri mutant KtKRS-5

<400> SEQUENCE: 12

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110
```

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Thr Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Val Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 13
<211> LENGTH: 1260
<212> TYPE: DNA
<213> ORGANISM: Artificial Sequence
<220> FEATURE:
<223> OTHER INFORMATION: Methanosarcina barkeri mutant KtKRS-5

<400> SEQUENCE: 13
atggataaaa aaccgctgga tgtgctgatt agcgcgaccg gcctgtggat gagccgtacc      60
ggcaccctgc ataaaatcaa acatcatgaa gtgagccgca gcaaaatcta tattgaaatg     120
gcgtgcggcg atcatctggt ggtgaacaac agccgtagct gccgtaccgc gcgtgcgttt     180
cgtcatcata ataccgcaa aacctgcaaa cgttgccgtg tgagcgatga agatatcaac     240
aactttctga cccgtagcac cgaaagcaaa aacagcgtga aagtgcgtgt ggtgagcgcg     300

```
ccgaaagtga aaaaagcgat gccgaaaagc gtgagccgtg cgccgaaacc gctggaaaat    360
agcgtgagcg cgaaagcgag caccaacacc agccgtagcg ttccgagccc ggcgaaaagc    420
accccgaaca gcagcgttcc ggcgtctgcg ccggcaccga gcctgacccg cagccagctg    480
gatcgtgtgg aagcgctgct gtctccggaa gataaaatta gcctgaacat ggcgaaaccg    540
tttcgtgaac tggaaccgga actggtgacc cgtcgtaaaa acgattttca gcgcctgtat    600
accaacgatc gtgaagatta tctgggcaaa ctggaacgtg atatcaccaa attttttgtg    660
gatcgcggct ttctggaaat taaaagcccg attctgattc cggcggaata tgtggaacgt    720
atgggcatta acaacgacac cgaactgagc aaacaaattt tccgcgtgga taaaaacctg    780
tgcctgcgtc cgatgctggc gccgaccctg tataactata cgcgtaaact ggatcgtatt    840
ctgccgggtc cgatcaaaat ttttgaagtg ggcccgtgct atcgcaaaga aagcgatggc    900
aaagaacacc tggaagaatt caccatggtt aactttgtgc aaatgggcag cggctgcacc    960
cgtgaaaacc tggaagcgct gatcaaagaa ttcctggatt atctggaaat cgacttcgaa    1020
attgtgggcg atagctgcat ggtgtatggc gataccctgg atattatgca tggcgatctg    1080
gaactgagca gcgcggtggt gggtccggtt agcctggatc gtgaatgggg cattgataaa    1140
ccgtggattg gcgcgggttt tggcctggaa cgtctgctga aagtgatgca tggcttcaaa    1200
aacattaaac gtgcgagccg tagcgaaagc tactataacg gcattagcac gaacctgtaa    1260
```

METHODS

The present application is filed pursuant to 35 U.S.C. 371 as a U.S. National Phase application of International Patent Application No. PCT/GB2010/001083, which was filed Jun. 2, 2010, claiming the benefit of priority to British Patent Application No. 0909645.4, which was filed on Jun. 4, 2009, and U.S. Provisional Patent Application No. 61/187,402, which was filed on Jun. 16, 2009. The entire text of the aforementioned applications is incorporated herein by reference in its entirety.

FIELD OF THE INVENTION

The invention relates to the production of polypeptide(s) having unnatural amino acids or derivatives incorporated which provide useful functional groups to said polypeptide(s). In particular the invention relates to the incorporation of aliphatic groups into a polypeptide.

BACKGROUND TO THE INVENTION

The genetic code of prokaryotic and eukaryotic organisms has been expanded to allow the in vivo, site-specific incorporation of over 20 designer unnatural amino acids in response to the amber stop codon. This synthetic genetic code expansion is accomplished by endowing organisms with evolved orthogonal aminoacyl-tRNA synthetase/ $tRNA_{CUA}$ pairs that direct the site-specific incorporation of an unnatural amino acid in response to an amber codon. The orthogonal aminoacyl-tRNA synthetase aminoacylates a cognate orthogonal tRNA, but no other cellular tRNAs, with an unnatural amino acid, and the orthogonal tRNA is a substrate for the orthogonal synthetase but is not substantially aminoacylated by any endogenous aminoacyl-tRNA synthetase.

The site-specific and homogeneous modification of recombinant proteins under physiological conditions is an important challenge. Cysteines and other amino acid residues in proteins can be specifically labeled by several methods(1), but site-specificity, as opposed to residue specificity(2, 3), is difficult to achieve.

Several phenylalanine derivatives can be site-specifically introduced into recombinant proteins in response to an amber codon (UAG) inserted into the corresponding gene using an evolved tyrosyl-tRNA synthetase-tRNACUA pair that is orthogonal in E. coli(4). Phenylalanine derivatives bearing alkynyl- azido- and keto-groups, that are bio-orthogonal in their chemical reactivity have been incorporated (5-8). However the introduction of aromatic amino acids at sites where aliphatic amino acids are naturally found may cause misfolding or loss of protein function; there is therefore a pressing need for methods to site-specifically incorporate aliphatic amino acids that contain bio-orthogonal chemical handles for use in protein labeling.

Use of a tRNA synthetase-tRNA pair for incorporation of novel amino acids into proteins has been performed in the art. The Methanosarcina barkeri MS Pyrrolysyl tRNA synthetase/tRNACUA (MbPylRS/MbtRNACUA) pair is a new orthogonal pair in E. coli(9, 10). We demonstrated that the MbPylRS/tRNACUA pair can be evolved to direct the efficient incorporation of unnatural amino acids into genetically determined sites in recombinant proteins(10) and several unnatural amino acids have now been incorporated by evolving this pair(11, 12).

Since unnatural amino acids destined for incorporation into recombinant proteins are added to cell cultures at 1-10 mM(9) it is important that they can be synthesized in gram quantities via concise, efficient syntheses. Yokoyama and coworkers recently reported the genetic incorporation of the aromatic, photoreactive lysine derivative Ne-(o-azidobenzyloxycarbonyl-lysine) using a mutant pyrrolysine synthetase/tRNA pair(11). However, the synthetic route, yield and NMR characterization of this amino acid were not reported. Very recently Chan and coworkers reported the incorporation of a direct pyrrolysine analog with an appended alkyne (14). The pyrrolysine analog was synthesized in 17% yield after 16 steps.

Shultz and Xie (Current Opinion in Chemical Biology 2005 volume 9 pages 548 to 554) disclose adding amino acids to the genetic repertoire. In the work reviewed by these authors, use is made of a naturally occurring tyrosyl amber suppressor. The active site of this tRNA synthetase was modified and then selected with the aim of excluding binding to tyrosine and with the aim of acquiring the property of binding to non-tyrosine amino acids. This work focused on binding to near neighbours of tyrosine such as tyrosine analogues. The tRNA synthetase mutants which were obtained represent the output from the sum of the selective processes used. Among other things, these required multiple rounds of selection for enrichment, followed by manual characterisation of the resulting candidates with the hope of finding specificity for a particular tyrosine analogue amongst the particular mutants obtained. It should be noted that these studies were purely confined to aromatic amino acid moieties.

Polycarpo et al (PNAS 2004 Vol 101 pages 12450-12454) disclose an animoacyl-tRNA synthetase that specifically activates pyrrolysine. In this study, it was investigated whether or not certain analogues of pyrrolysine were substrates for the pyrrolysine tRNA synthetase. Pyrrolysine is an amino acid which is not conventionally regarded as one of the 20 essential amino acids, but can be found in certain organisms such as Methanococcus bacteria. These studies used naturally occurring tRNA-tRNA synthetase pairs from Methanococcus bacteria. The experimental system was arranged as an E. coli host cell comprising a lac Z gene bearing an amber mutation. In this manner, colonies could be easily scored for translation through the amber codon by simply looking for lac Z activity by conventional X-gal staining. This study attempted to discover what analogues of pyrrolysine could be incorporated by the pyrrolysine tRNA synthetase. It was an aim to try to understand what elements of the chemical structure of pyrrolysine were recognised by the tRNA synthetase being studied. For example, carbon atoms were added or removed to pyrrolysine to create analogues, and certain bonds within the pyrrolysine molecule were rearranged to create other analogues, and the incorporation of these analogues by the pyrrolysine tRNA synthetase was studied. The most likely interpretation of the studies disclosed by Polycarpo is that some of the analogues of pyrrolysine which were used were indeed incorporated by the tRNA synthetase. Although no formal proof of incorporation in a molecular sense was presented (the data were based on functional phenotypic readout of lac Z activity), on the basis of what is disclosed it would be reasonable to conclude that some of the pyrrolysine analogues studied were indeed incorporated into proteins using their system. It should be noted that all of the chemical analogues of pyrrolysine studied were aromatic molecules.

Fekner, Li, Lee and Chan (Angew Chem Int Ed 2009 vol 48 pages 1633-1635) disclose a pyrrolysine analogue for protein click chemistry. In particular, a direct pyrrolysine analogue is disclosed, which comprises aromatic carbon groups. This aromatic compound is then incorporated into polypeptide. The techniques disclosed in this paper comprise at least about ten separate chemical synthetic steps, which is very labour intensive and time consuming. The techniques described suffer from the drawback of low yields. Overall this technique is impractical to perform routinely in the manufacture of polypeptides of interest.

Yanagisawa et al. disclose multistep engineering of pyrrolysyl-tRNA synthetase to genetically encode N-epsilon-(o-azidobenzyloxycarbonyl) lysine for site specific protein modification. It should be noted that this corresponds to a lysine-aromatic-azide arrangement, in other words the molecule incorporated into the polypeptide comprises aromatic carbon groups. Moreover, these aromatic carbon groups are photosensitive, which requires production in darkness or in extremely low light conditions. This is labour intensive and costly since numerous synthetic steps and apparatus must be operated under these conditions. This study also involves mutated tRNA synthetase.

The present invention seeks to overcome problem(s) associated with the prior art.

SUMMARY OF THE INVENTION

The inventors teach the use of a permissive tRNA synthetase in order to incorporate certain unnatural amino acids into proteins of interest. In particular, the present inventors teach the incorporation of aliphatic or straight chain carbon backbone amino acids capable of supporting alkyne-azide bonding into a protein of interest. The prior art has been exclusively concerned with the incorporation of aromatic molecules into proteins of interest.

The present inventors realised that it is not realistic or indeed desirable to replace amino acids in a protein of interest exclusively with aromatic amino acids such as tyrosines. Such a strategy is almost certain to destroy protein functionality. Thus, there is a need in the art for an alternative incorporation system which avoids the problematic chemical properties of aromatic compounds when making proteins incorporating altered or unnatural amino acids. From another perspective, the inventors provide methods for incorporating altered or unnatural amino acids into a polypeptide of interest which are based on a non-aromatic amino acid scaffold. In addition to this key structural difference, it should be noted that the presentation of the functional group such as the alkyne group is different in the present invention from what has been attempted before in the art.

Incorporation of aliphatic or straight chain modified or unnatural amino acids into proteins in the prior art has typically been accomplished by mass action or pressure of incorporation, i.e. by techniques which aim to overwhelm the normal cellular machinery with the unnatural or modified aliphatic amino acid, and thereby achieve incorporation by a stifling or suffocation of the ordinary translation machinery, thereby leading to incorporation of the desired amino acid into the polypeptide of interest. By contrast, the present invention is a specific and targeted incorporation technique, directed at specific codons, which may include among others quadruplet codons or suppressor codons, most suitably at a suppressor codon such as the amber suppressor codon.

These and other advantages of the invention will be discussed more fully below.

Thus, in one aspect, the invention provides a method of making a polypeptide comprising an orthogonal functional group, said orthogonal functional group being comprised by an aliphatic amino acid or amino acid derivative, said method comprising providing a host cell;
providing a nucleic acid encoding the polypeptide of interest;
providing a tRNA-tRNA synthetase pair orthogonal to said host cell;
adding an amino acid or amino acid derivative comprising the orthogonal functional group of interest, wherein said amino acid or amino acid derivative is a substrate for said orthogonal tRNA synthetase, wherein said amino acid or amino acid derivative has an aliphatic carbon backbone; and
incubating to allow incorporation of said amino acid or amino acid derivative into the polypeptide of interest via the orthogonal tRNA-tRNA synthetase pair.

An orthogonal functional group is a bio-orthogonal chemical group or chemical 'handle' for use in bonding of the polypeptide to another chemical moiety such as a label or another polypeptide. The orthogonal functional group is suitably orthogonal in the sense of not naturally occurring in polypeptides. Thus it may be convenient to regard the orthogonal functional group as an unnatural functional group, in particular unnatural in the context of polypeptides. Examples of orthogonal functional groups in the context of polypeptide manufacture include alkynes, azides, and aliphatic ketones.

It is important that the amino acid or amino acid derivative comprises an aliphatic moiety. This is the first time incorporation of such aliphatic moieties into polypeptides has been taught according to the present invention. Suitably the amino acid or amino acid derivative may consist of an aliphatic moiety.

Suitably the amino acid or amino acid derivative does not comprise an aromatic moiety. Aromatics can compromise polypeptide function. Aromatics are not suitable for substitution into certain sites in polypeptides. Many aromatics are photosensitive. These drawbacks are advantageously avoided by the invention as applied to aliphatic orthogonal functional groups.

Suitably incorporation is mediated by an amber codon specified by said nucleic acid. Clearly in this embodiment the tRNA should recognise the amber codon and the tRNA synthetase should be capable of charging said tRNA.

Suitably the functional group is an alkyne group.
Suitably the functional group is an azide group.
Suitably the functional group is an aliphatic ketone.
Suitably the amino acid or amino acid derivative is or is derived from lysine.
Suitably the orthogonal tRNA-tRNA synthetase pair are a cognate pair capable of acting on pyrrolysine.
Suitably the orthogonal tRNA-tRNA synthetase pair have sequences corresponding to the wild type sequences of the organism in which they naturally occur.
Suitably the tRNA-tRNA synthetase pair is MbtRNACUA and MbPylRS.
Suitably the MbtRNACUA comprises the nucleotide sequence of SEQ ID NO:3.
Suitably the MbPylRS comprises the amino acid sequence of SEQ ID NO:1.
Suitably the host cell is *E. coli*.

In another aspect, the invention relates to a polypeptide, preferably a polypeptide produced as described above, said polypeptide comprising an orthogonal functional group, said orthogonal functional group being comprised by an aliphatic amino acid or amino acid derivative, said orthogonal functional group being selected from the group consisting of alkyne, azide and aliphatic ketone.

In another aspect, the invention relates to a polypeptide, preferably a polypeptide produced as described above, said polypeptide comprising an amino acid selected from the group consisting of N6-[(2-propynyloxy)carbonyl]-L-lysine, N6-[(2-azidoethoxy)carbonyl]-L-lysine and (S)-2-amino-6-((pent-4-enyloxy)carbonylamino)hexanoic acid.

In another aspect, the invention relates to a tRNA synthetase having the amino acid sequence of SEQ ID NO:4, SEQ ID NO:6, SEQ ID NO:8, SEQ ID NO:10 or SEQ ID NO:12. Suitably in the method as described above, the tRNA synthetase is a tRNA synthetase having the amino acid sequence of SEQ ID NO:4, SEQ ID NO:6, SEQ ID NO:8, SEQ ID NO:10 or SEQ ID NO:12.

In another aspect, the invention relates to a nucleic acid comprising the nucleotide sequence of SEQ ID NO:5, SEQ ID NO:7, SEQ ID NO:9, SEQ ID NO:11 or SEQ ID NO:13. Suitably in the method as described above, the tRNA synthetase is a tRNA synthetase encoded by the nucleotide sequence of SEQ ID NO:5, SEQ ID NO:7, SEQ ID NO:9, SEQ ID NO:11 or SEQ ID NO:13.

In another aspect, the invention relates to an amino acid molecule comprising an aliphatic functional group orthogonal to *E. coli*.

In another aspect, the invention relates to an amino acid molecule as described above wherein said aliphatic functional group comprises an alkyne, azide, or aliphatic ketone group.

In another aspect, the invention relates to an amino acid molecule as described above wherein said amino acid is selected from the group consisting of N6-[(2-propynyloxy)carbonyl]-L-lysine, N6-[(2-azidoethoxy)carbonyl]-L-lysine and (S)-2-amino-6-((pent-4-enyloxy)carbonylamino) hexanoic acid.

DEFINITIONS

The term 'comprises' (comprise, comprising) should be understood to have its normal meaning in the art, i.e. that the stated feature or group of features is included, but that the term does not exclude any other stated feature or group of features from also being present.

DETAILED DESCRIPTION OF THE INVENTION

The invention provides genetic encoding and labeling of aliphatic azides and alkynes in recombinant proteins via a pyrrolysyl-tRNA synthetase tRNAcua pair and click chemistry. In other words, the invention provides genetic encoding and labeling of simple azides and alkynes in recombinant proteins via a pyrrolysyl-tRNA synthetase tRNAcua pair and click chemistry.

We demonstrate that an orthogonal *Methanosarcina barkerii* MS pyrrolysyl-tRNA synthetase/tRNACUA pair directs the efficient, site-specific incorporation of N6-[(2-propynyloxy)carbonyl]-L-lysine, containing a carbon-carbon triple bond, and N6-[(2-azidoethoxy)carbonyl]-L-lysine, containing an azido group, into recombinant proteins in host cells such as *Escherichia coli* cells. Proteins containing the alkyne functional group may be labelled with an azido biotin and an azido fluorophore, via copper catalysed [3+2] cycloaddition reactions, to produce the corresponding triazoles in good yield.

The methods of the invention are useful for the site-specific labelling of recombinant proteins. The methods of the invention and may also be combined with mutually orthogonal methods of introducing unnatural amino acids into proteins as well as with chemically orthogonal methods of protein labelling. This advantageously allows the site specific incorporation of multiple distinct probes into proteins. This also has the benefit of facilitating the control of protein topology and/or structure by intramolecular orthogonal conjugation reactions.

The *Methanosarcina barkeri* PylS gene encodes the MbPylRS tRNA synthetase protein. The *Methanosarcina barkeri* PylT gene encodes the MbtRNA$_{CUA}$ tRNA.

Sequence Homology/Identity

Although sequence homology can also be considered in terms of functional similarity (i.e., amino acid residues having similar chemical properties/functions), in the context of the present document it is preferred to express homology in terms of sequence identity.

Sequence comparisons can be conducted by eye or, more usually, with the aid of readily available sequence comparison programs. These publicly and commercially available computer programs can calculate percent homology (such as percent identity) between two or more sequences.

Percent identity may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example in an otherwise identical pair of sequences, one insertion or deletion will cause the following amino acid residues to be put out of alignment, thus potentially resulting in a large reduction in percent homology (percent identity) when a global alignment (an alignment across the whole sequence) is performed. Consequently, most sequence comparison methods are designed to produce optimal alignments that take into consideration possible insertions and deletions without penalising unduly the overall homology (identity) score. This is achieved by inserting "gaps" in the sequence alignment to try to maximise local homology/identity.

These more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum percent homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package, FASTA (Altschul et al., 1990, J. Mol. Biol. 215: 403-410) and the GENEWORKS suite of comparison tools.

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62. Once the software has produced an optimal alignment, it is possible to calculate percent homology, preferably percent sequence identity. The software typically does this as part of the sequence comparison and generates a numerical result.

In the context of the present document, a homologous amino acid sequence is taken to include an amino acid sequence which is at least 15, 20, 25, 30, 40, 50, 60, 70, 80 or 90% identical, preferably at least 95 or 98% identical at the amino acid level. Suitably this identity is assessed over at least 50 or 100, preferably 200, 300, or even more amino acids with the relevant polypeptide sequence(s) disclosed herein, most suitably with the full length progenitor (parent) tRNA synthetase sequence. Suitably, homology should be considered with respect to one or more of those regions of the sequence known to be essential for protein function rather than non-essential neighbouring sequences. This is especially important when considering homologous sequences from distantly related organisms.

Most suitably sequence identity should be judged across at least the contiguous region from L266 to C313 of the amino acid sequence of MbPyIRS, or the corresponding region in an alternate tRNA synthetase.

The same considerations apply to nucleic acid nucleotide sequences, such as tRNA sequence(s).

Reference Sequence

When particular amino acid residues are referred to using numeric addresses, the numbering is taken using MbPyIRS (*Methanosarcina barkeri* pyrrolysyl-tRNA synthetase) amino acid sequence as the reference sequence (i.e. as encoded by the publicly available wild type *Methanosarcina barkeri* PyIS gene). This is to be used as is well understood in the art to locate the residue of interest. This is not always a strict counting exercise—attention must be paid to the context. For example, if the protein of interest is of a slightly different length, then location of the correct residue in that sequence corresponding to (for example) Y271 may require the sequences to be aligned and the equivalent or corresponding residue picked, rather than simply taking the 271st residue of the sequence of interest. This is well within the ambit of the skilled reader.

Mutating has it normal meaning in the art and may refer to the substitution or truncation or deletion of the residue, motif or domain referred to. Mutation may be effected at the polypeptide level e.g. by synthesis of a polypeptide having the mutated sequence, or may be effected at the nucleotide level e.g. by making a nucleic acid encoding the mutated sequence, which nucleic acid may be subsequently translated to produce the mutated polypeptide. Where no amino acid is specified as the replacement amino acid for a given mutation site, suitably a randomisation of said site is used, for example as described herein in connmection with the evolution and adaptation of tRNA synthetase of the invention. As a default mutation, alanine (A) may be used. Suitably the mutations used at particular site(s) are as set out herein.

A fragment is suitably at least 10 amino acids in length, suitably at least 25 amino acids, suitably at least 50 amino acids; suitably at least 100 amino acids, suitably at least 200 amino acids, suitably at least 250 amino acids, suitably at least 300 amino acids, suitably at least 313 amino acids, or suitably the majority of the tRNA synthetase polypeptide of interest.

Polypeptides of the Invention

Suitably the polypeptide manufactured according to the present invention may be any polypeptide of interest. Suitably this is made using nucleic acid encoding it as described herein.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Vectors of the invention may be transformed or transfected into a suitable host cell as described to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

Protein Expression and Purification

Host cells comprising polynucleotides of the invention may be used to express proteins of the invention. Host cells may be cultured under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Proteins of the invention can be extracted from host cells by a variety of techniques known in the art, including enzymatic, chemical and/or osmotic lysis and physical disruption.

Optimisation

Unnatural amino acid incorporation in in vitro translation reactions can be increased by using S30 extracts containing a thermally inactivated mutant of RF-1. Temperature sensitive mutants of RF-1 allow transient increases in global amber suppression in vivo. Increases in tRNACUA gene copy number and a transition from minimal to rich media may also provide improvement in the yield of proteins incorporating an unnatural amino acid in E. coli.

Advantages

Suitably the tRNA-tRNA synthetase pair employed in the invention does not recognise any of the 20 naturally occurring amino acids. This has the advantage of making it orthogonal to the ordinary host cell translation machinery.

In many embodiments, suitably the tRNA-tRNA synthetase pair employed correspond to the wild type or unaltered sequences of the organism from which they are derived. This has the advantage of avoiding the need to reassign the active site of a tRNA synthetase to a new amino acid. In other words, in many embodiments advantageously the invention does not require the use of altered tRNA synthetase molecules such as mutated tRNA synthetase molecules. Thus, in these embodiments it is an advantage of the invention that no evolution of the tRNA synthetase molecule is required. The inventors disclose a novel permissivity of the natural tRNA synthetase used, such as the MB tRNA synthetase for pyrrolysine. However, notwithstanding this, it will be apparent that evolution/alteration of the tRNA-tRNA synthetase pair employed may offer advantages or indeed may be required for incorporation of certain embodiments featuring particular functional groups or amino acids/amino acid derivatives—one example of this is in the incorporation of aliphatic ketone group(s) which are discussed in more detail below. Thus, for at least the incorporation of alkyne and/or azide groups into a polypeptide according to the present invention, suitably the tRNA-tRNA synthetase pair employed correspond to the wild type or unaltered sequences of the organism from which they are derived.

When the invention is applied to the incorporation of aliphatic ketone group(s), suitably the wild type tRNA synthetase (SEQ ID NO:1 or SEQ ID NO:2) is not used but rather the tRNA synthetase used comprises the amino acid sequence of one or more of SEQ ID NO:4, SEQ ID NO:6, SEQ ID NO:8, SEQ ID NO:10 or SEQ ID NO:12. The amino acid sequences of KtKRS2 (SEQ ID NO:6) and KtKRS3 (SEQ ID NO:8) are identical; these differ only in the nucleotide sequences of SEQ ID NO:7 and SEQ ID NO:9 respectively. Most preferred tRNA synthetase for ketone incorporation is SEQ ID NO:6 or SEQ ID NO:8; most preferred nucleotide sequence of tRNA synthetase for ketone incorporation is SEQ ID NO:7 or SEQ ID NO:9.

tRNA synthetase comprising the amino acid sequence of one or more of SEQ ID NO:4, SEQ ID NO:6, SEQ ID NO:8, SEQ ID NO:10 or SEQ ID NO:12 may also be used to incorporate azide or alkyne; however use of these sequences for alkyne/azide incorporation may be sub-optimal and thus suitably the tRNA synthetase used for azide or alkyne incorporation suitably comprises the amino acid sequence of SEQ ID NO:1 (or nucleotide sequence of SEQ ID NO:2).

For all embodiments suitably the tRNA used comprises the sequence of SEQ ID NO:3.

It is an advantage of the invention that it is applied to aliphatic/straight carbon chain amino acid derivatives. Prior art techniques have been confined to aromatic amino acid derivatives. Thus, it is a further advantage of the invention that the presentation of the reactive group such as the alkyne group is different to what has been attempted before, in particular it advantageously avoids presentation of the alkyne group on an aromatic molecule.

It is an advantage that the techniques of the invention provide simple methods comprising only a small number of steps for production of the protein of interest.

It is an advantage of the invention that the techniques are easily applied to the manufacture of gram amounts of the polypeptide of interest. Prior art attempts have tended to rely on very complicated multi-step syntheses, having correspondingly low yields, which are difficult or impossible to apply industrially. By contrast, the methods of the present invention permit substantial and industrially useful quantities of polypeptides to be manufactured in a simplified method.

It is an advantage of the invention that the moieties incorporated into the polypeptides of interest avoid the pyrrolysine ring structure. The pyrrolysine ring structure is larger than and quite different from the molecular structure of naturally occurring amino acids. Therefore, the effects of incorporation of this molecular entity into polypeptides of interest remain unclear and may be problematic. The present invention advantageously avoids such problems.

It is an advantage of the invention that the molecular entities being incorporated are photostable. Photosensitive molecules require extremely careful handling, oblige the operators to work in low light conditions, and are extremely labile and difficult to work with. These drawbacks are advantageously alleviated by the methods of the present invention.

It is an advantage of the invention that for the first time the site-specific incorporation of aliphatic functional groups (such as alkynes, azides, aliphatic ketones) into a polypeptide of interest is provided.

The labelling of lysine residues has been applied in the prior art, such as in connection with bioconjugation of proteins. However, site-specificity for the labelling of lysine residues can not be achieved with prior art technologies. We described an unnatural amino acid mutagenesis technology that addresses this problem.

Our invention is in contrast to prior art technologies which employ aromatic amino acids.

Substitutions

Suitably, the invention is used to replace any naturally occurring amino acid other than tryptophan, phenylalanine or tyrosine.

Suitably, the invention is used to replace any non-aromatic amino acid.

Suitably, the invention is used to replace any aliphatic amino acid.

Suitably, the invention is used to replace an amino acid selected from lysine, aspartic acid, serine, cysteine, threonine, valine or isoleucine.

Suitably, the invention is used to replace any of serine, cysteine, threonine, valine or isoleucine.

Most suitably, the invention is used to replace valine or isoleucine.

The invention may be used to replace a charged amino acid such as lysine or aspartic acid.

The invention may be used to replace a hydroxyl-type amino acid such as serine, cysteine, threonine.

Most suitably, the invention may be used to replace a hydrocarbon-type amino acid such as valine or isoleucine.

In the present invention the term 'replace' refers to substitution or mutation, for example by replacing the codon for the amino acid being substituted with a codon to direct incorporation of amino acid or amino acid derivative by the orthogonal tRNA. Thus the 'replacement' is suitably achieved with reference to the starting sequence by alteration of the coding sequence to direct incorporation by the orthogonal tRNA/tRNA synthetase, rather than referring to excision of an amino acid from the synthesised polypeptide.

Functional Groups

It will appreciated that many of the embodiments described to exemplify the invention relate to the incorporation of an alkyne group onto the polypeptide of interest. This is advantageous in permitting the binding to another entity such as a label or other polypeptide via an azide linkage present on said label or other polypeptide. However, it will be appreciated by the skilled reader, that the reversal of the functional groups on the polypeptide or label (or the polypeptide or second polypeptide) is a variant which is intended to be within the scope of the present invention. The conventional chemistry (eg, "click chemistry") as is well-known in the art through the publications of Sharpless et al can easily be carried out independent of the placement of the alkyne or azide groups on the target polypeptide or on the label/second polypeptide as appropriate.

Thus, it will be appreciated by the skilled reader that the invention equally embraces the incorporation of azide groups or other reactive groups capable of joining molecules via an alkyne functional group into the polypeptide of interest.

'Click chemistry' refers generally to the well known chemistry of ligation/addition reactions. In particular, the joining of azides to alkynes is an especially useful element of click chemistry which may be applied to the polypeptides produced according to the present invention. For example, Rostovtsev et al. (2002 Angew Chem Int Ed vol 41 pages 2596-2599) describe in detail how a range of such reactions may be performed. Moreover, Kolb et al. (Angew Chem Int Ed 2001 vol 40 pages 2004-2021) present an extensive review of this area of combinatorial chemistry and its application to many diverse systems. The polypeptides of the invention may suitably be further modified in accordance with such click chemistry. Indeed, it is a key industrial application of the invention that polypeptides may be produced according to the present invention for modification via click chemistry, enabling a range of labels or other chemical moieties to be easily and conveniently attached to defined locations in the polypeptide, as well as enabling intra-molecular bonding between different regions of the polypeptide if desired.

In some embodiments the functional group may be other than an alkyne or an azide, for example it may be an aliphatic ketone.

Amino Acid Derivatives

The invention also relates to certain novel amino acids/amino acid derivatives. In particular, these are as described in the example section below and in the accompanying figures.

In addition, the invention embraces methods of making these amino acids/amino acid derivatives.

tRNA-tRNA Synthetase Pairs

Most preferred are tRNA-tRNA synthetase pairs which do not recognise any of the 20 naturally occurring amino acids.

Most suitably, the tRNA-tRNA synthetase pair is derived from a *Methanococcus* bacterium. Most suitably, the tRNA-tRNA synthetase pair is derived from *Methanococcus barkerii* bacterium.

It will be appreciated that corresponding or cognate tRNA or tRNA synthetases may be combined from different species of *Methanococcus* bacterium. For example, it may be possible to use a pyrrolysine tRNA from *M. barkerii* together with a pyrrolysyl tRNA synthetase from *Methanococcus janaschii*. The functionality of such pairings is easily tested according to the methods set out herein, e.g. by combining the different components in a host cell and analysing for intact polypeptide of interest produced.

Codons

In principle, any codon which is orthogonal to the host cell being used may be employed in the invention, for example, four base codons (quadruplet codons) may be used. Most suitable quadruplet codons are those which are direct derivatives of triplet codons, such as CCCU, CCCC, or AGGA. Most preferred is AGGA.

Most suitably, the codon used to direct unnatural or modified amino acid incorporation according to the invention is an amber codon.

Amino Acid Derivatives

Suitably, the amino acid derivative is not an amide.

Suitably, the amino acid derivative used comprises a carbonyl and an oxygen moiety. Most suitably, the moiety comprising carbonyl and oxygen is a carbamate.

Most suitably, the functional group incorporated is an alkyne group.

Suitably, an azide functional group may be incorporated. When the functional group is an azide, the moiety used to incorporate it is suitably as described above, most suitably a carbamate.

Further Applications

It will be apparent to the skilled reader that the invention finds application in any setting where it is desired to join a polypeptide to another molecular entity. For example, it may be used in the labelling of polypeptides of interest according to standard chemistry (eg click chemistry). Moreover, it may be used to join polypeptides together to link them into dimers or higher order chains. In this embodiment, an alkyne group might be incorporated into a first polypeptide, and an azide group incorporated into a second polypeptide. The alkyne and azide groups may then be reacted together, leading to a covalently joined single molecule comprising the first and second polypeptides. This has advantages over conventional methods of linking polypeptides such as via cysteine bridges, since the covalent bonding produced according to the present invention is not sensitive to destruction by redox reactions.

Moreover, it will be apparent that the invention may be used to produce linkages within single polypeptides themselves. In this embodiment, a functional group such as an alkyne group might be incorporated in a first position in a polypeptide, and a second functional group such as an azide group would be incorporated into a second position of a polypeptide. Thus, by reacting the first and second functional groups together, a cyclysed or looped polypeptide is advantageously produced. This may have application in the stabilization of polypeptides, such as hormones or other linked or bridged polypeptides.

The invention may be used to incorporate more than one orthogonal functional group into the polypeptide of interest. This may be more than one of the same orthogonal functional group, for example by using more than one substitution in the nucleic acid encoding the polypeptide of interest to permit incorporation at more than one site in said polypeptide.

Alternatively this may be one or more substitutions at two or more sites in the polypeptide, wherein said substitutions may be for different orthogonal functional groups. For example, it may be desired to incorporate more than one type of orthogonal functional group into a single polypeptide. In such embodiments suitably a second orthogonal tRNA-tRNA synthetase pair is used to incorporate the second orthogonal functional group; suitably said second orthogonal tRNA-tRNA synthetase pair recognises a different orthogonal codon in the nucleic acid encoding the polypeptide of interest so that the two or more orthogonal functional groups can be specifically incorporated into different defined sites in the polypeptide in a single manufacturing step. An application of this is for example in the cyclisation of the polypeptide; in this embodiment a first alkyne group may be incorporated into a first position and an azide group may be incorporated into a second position; after manufacture of the polypeptide then the alkyne and azide groups may be reacted together forming a covalent bond joining the two parts of the polypeptide. Other similar applications may be envisaged by the skilled operator.

In addition, since MbPyIRS does not recognize the anticodon of MbtRNACUA it is further possible to combine evolved MbPyIRS/MbtRNA pairs with other evolved orthogonal aminoacyl-tRNA synthetase/tRNACUA pairs, and/or with orthogonal ribosomes with evolved decoding properties to direct the efficient incorporation of multiple distinct useful unnatural amino acids in a single protein.

BRIEF DESCRIPTION OF THE FIGURES

FIG. 2: The increase in full length protein synthesis as a function of amino acid concentration.

FIG. 3: The structures of the biotin azide 5 and By3 azide 6 used The invention is now described by way of example. These examples are intended to be illustrative, and are not intended to limit the appended claims.

EXAMPLES

Example 1

Here we describe the synthesis and genetic incorporation of aliphatic azides and alkynes into proteins using the natural MbPyIRS/tRNACUA pair and the efficient bioorthogonal labeling of these amino acids using [3+2] cycloaddition ('click') chemistry(13).

Figure 1:
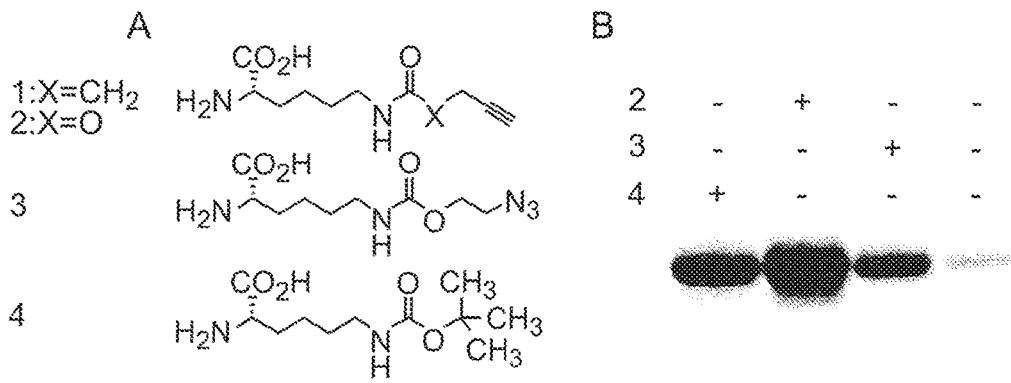
FIG. 1 shows: A. Alkyne 1, 2 or azide 3. B. Ni-NTA Purified myoglobin-his6 from cells containing the PyIRS/tRNACUA orthogonal pair. 4 is a known efficient substrate for the PyIRS/tRNACUA pair.

We designed and synthesized aliphatic, photostable amino acids 1 and 2 that link the alkyne functional group to a lysine residue via an amide or carbamate bond (FIG. 1). These amino acids were synthesized in 2 steps and 70-80% yield from commercially available material (Supplementary Scheme 1, Supplementary FIG. 1 & Supplementary Methods).

To investigate whether 1 and 2 are substrates for the MbPyIRS/tRNACUA pair, we transformed E. coli with pBKPylS10 (which encodes MbPyIRS) and pMyo4TAGPylT-his610 (which encodes MbtRNACUA and a C-terminally hexahistidine tagged myoglobin gene with an amber codon at position 4). We added 1 or 2 (1 mM) to log phase cells and induced myoglobin-his6 expression. While in the presence of 1, only background levels of myoglobin-his6 were purified by Ni-NTA chromatography, full-length myoglobin was purified in good yield (2 mg/L, comparable to that for other unnatural amino acids(5,10)) after expression in the presence of 2; indicating that 2 but not 1 is incorporated by the MbPyIRS/tRNACUA pair. This may reflect the greater flexibility of the carbamate linkage. The yield of protein containing 2 was not improved by efforts to evolve the enzyme but was increased 5-fold by increasing the concentration of 2 7.5 fold (Supplementary FIG. 2A).

Previous work on genetically encoding alkynes in E. coli used LC-coupled to MS or MS/MS of tryptic fragments to demonstrate the incorporation(7, 11, 14). Since the ionization of closely related tryptic peptides may be very different it is not possible to assess the fidelity of incorporation via these methods. To demonstrate that 2 is incorporated with high fidelity and without modification by the cell(10) we used total protein electrospray ionization mass spectrometry (ESI-MS). Myoglobin-his6 incorporating 2 has the expected mass (found: 18477.5±1 Da, expected: 18478.2 Da, Supplementary FIG. 2B). These experiments demonstrate that 2 can be site-specifically incorporated into recombinant proteins in good yield and with high selectivity.

To investigate if the carbamate linkage provides a general route to the incorporation of other functional groups suitable for bioconjugation, we synthesized a simple aliphatic azide 3 (2 steps, 80% yield, Supplementary Scheme 1 and Supplementary Methods). Protein expression and ESI-MS (FIG. 1, Supplementary FIG. 2C) experiments demonstrate that 3 is site-specifically incorporated into proteins in good yield (3 mg/L) using the MbPyIRS/MbtRNACUA pair.

To demonstrate that recombinant proteins containing the alkyne amino acid 2 can be site-specifically labeled with azido-probes (via a copper catalysed Huisgen [3+2] cycloaddition reaction(13)) myoglobin-his6 bearing 2 at position 4 was treated with the biotin azide 5 or a fluorophore (By3) azide 6 (Supplementary FIG. 3), in the presence CuSO4, 4,7-diphenyl-1,10-phenanthrolinedisulfonic acid disodium salt, and ascorbate in sodium phosphate buffer (pH 8.3) 15.

In control experiments myoglobin-his6 bearing 3 at position 4 was treated identically. After 18 h, the purified labeling reactions were probed (FIG. 2A). These experiments demonstrate the specific labeling of the alkyne containing protein.

Previous work has visualized protein labeling by gel-based methods alone(7, 11, 14), which does not allow quantification of labeling efficiency. ESI-MS of our purified labeling reaction (FIG. 2B) demonstrates a labeling efficiency of 90-100%. Quantification of the ratio of biotin or By3 to protein in purified samples provides independent confirmation of the labeling efficiency (Supplementary Methods).

In conclusion we demonstrate the efficient synthesis and site-specific, genetically encoded incorporation of aliphatic amino acids bearing a carbon-carbon triple-bond and/or bearing an azido group into recombinant proteins. We also demonstrate the near-quantitative on-protein labeling of the alkyne. In contrast to previous work(11, 14) the amino acids can be synthesized in just 2-steps in excellent yield and site-specifically incorporated.

CONCLUSIONS AND FURTHER APPLICATIONS

Unlike prior art techniques such as disclosed by Schultz we began with an orthogonal synthetase/tRNA pair that does not use the natural amino acids in *E. coli* and this allowed us to discover useful unnatural amino acids that the synthetase will use as substrates without the need for a series of enzyme evolution steps, at least for alkyne and azide incorporation.

In contrast to the aromatic azides previously incorporated by the prior art Schultz(5) or Yokoyama (11) techniques the aliphatic azide we have incorporated is photostable and is therefore easy to handle.

The genetically encoded alkyne 2 can be specifically and efficiently labeled with azides that introduce biotin or fluorescent groups, and in contrast to previous reports (7, 11, 14) we have explicitly demonstrated and quantified the efficient conjugation of probes to the genetically encoded amino acid.

Since many protein therapeutics are conjugated in a residue specific manner to polyethylene glycols through lysine(16) the method of the invention advantageously provides a direct route to discovering site-specifically modified versions of these therapeutics that are more efficacious.

The labelling method is compatible with, and orthogonal to cysteine labelling and finds utility in introducing two distinct labels into a single protein for fluorescence resonance energy transfer (FRET) experiments to probe protein function, structure and dynamic behaviour, as well as in other applications.

Moreover, since this synthetase tRNA pair is functional and orthogonal in eukaryotic cells(12) it is possible to apply the methods of the invention to the labelling of proteins produced in, and displayed on, eukaryotic cells.

The alkyne 2 and azide 3 are incorporated using a synthetase and tRNA pair that is mutually orthogonal in its aminoacylation specificity to the MjTyrRS/tRNACUA pair that has been used to incorporate a range of aromatic unnatural amino acids(4). Thus it may be useful to incorporate 2 or 3 in combination with genetically encoded aromatic amino acids, including previously incorporated azides(5) and alkynes(7), at distinct sites in recombinant proteins using suitably altered combinations of synthetase/tRNA pairs and evolved orthogonal ribosomes(17). This will allow the formation of directional intramolecular crosslinks to constrain protein structure and may allow for the genetic selection of enhanced protein stability and function.

Example 2: Incorporation of Aliphatic Ketone

Figure 5:
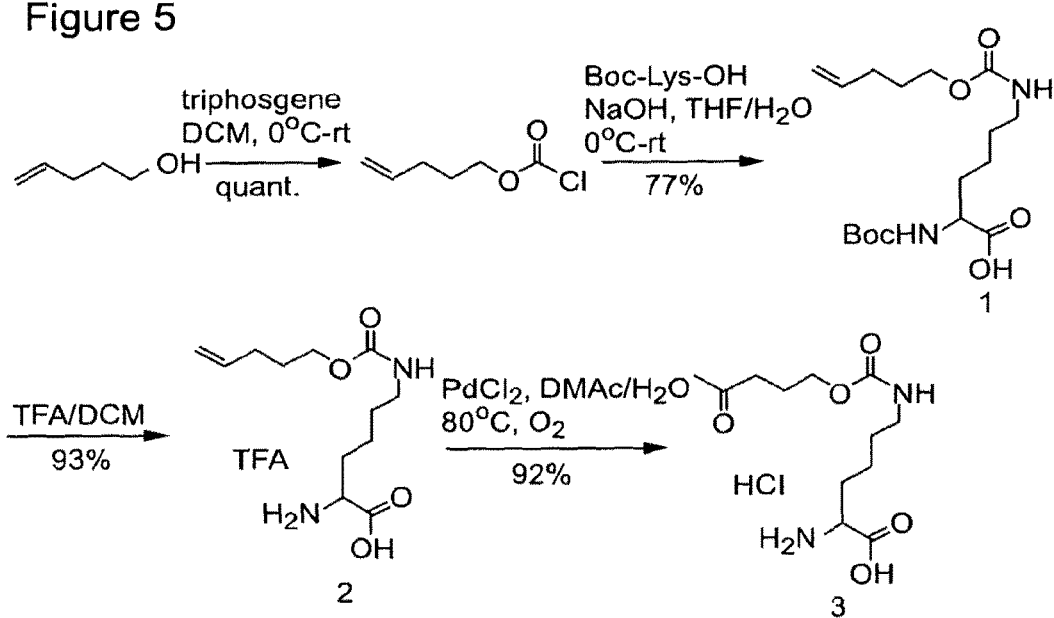
FIG. 5 shows chemical synthesis of exemplary amino acid derivative bearing aliphatic ketone

A suitable amino acid/derivative bearing aliphatic ketone for incorporation according to the present invention is shown in FIG. 5.

An exemplary synthesis is described in detail below:

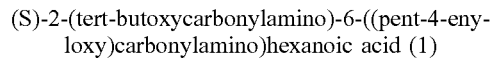
(S)-2-(tert-butoxycarbonylamino)-6-((pent-4-enyloxy)carbonylamino)hexanoic acid (1)

To a solution of 4-pentenyl alcohol (100 mg, 1.16 mmol) in DCM (1 mL) at 0° C. was added triphosgene (381 mg, 1.27 mmol). After the reaction was stirred for 8 h, the solvent was evaporated without heating and the residue dried under vacuum for 1 h. The prepared 4-pentenyl chloroformate was then added directly to a solution of Boc-Lys-OH (370 mg, 1.5 mmol) in $H_2O$:THF (5 mL:5 mL), at 0° C. containing NaOH (120 mg, 3 mmol). The reaction was stirred for 8 h, allowing it to warm to r.t. The reaction was subsequently acidified with cold 1 M HCl (20 mL) and extracted with EtOAc (25 mL). The organic layer was dried over $Na_2SO_4$, filtered and evaporated, affording 1 in 77% yield (350 mg, 0.98 mmol). $^1$H NMR ($CDCl_3$): δ=1.19-2.01 (m, 19H), 2.95 (m, 2H), 3.92 (m, 2H), 4.13 (m, 1H), 4.78 (m, 2H), 5.73 (m, 1H).

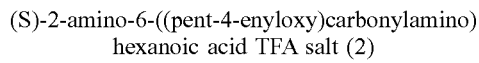
(S)-2-amino-6-((pent-4-enyloxy)carbonylamino) hexanoic acid TFA salt (2)

Compound 1 (350 mg, 0.98 mmol) was dissolved in DCM:TFA (3 mL:3 mL) and the reaction was allowed to stir at r.t. for 40 min. The solvents were subsequently evaporated and the residue was precipitated into $Et_2O$, giving 2 in 93% yield (323 mg, 0.91 mmol). $^1$H NMR ($D_2O$) δ=1.12-1.95 (m, 10H), 2.84-3.18 (m, 3H), 3.85 (m, 2H), 4.65-4.92 (m, 2H), 5.68 (m, 1H).

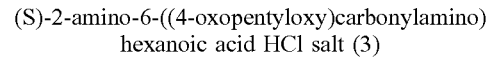
(S)-2-amino-6-((4-oxopentyloxy)carbonylamino) hexanoic acid HCl salt (3)

Compound 2 (320 mg, 0.91 mmol) was dissolved in 1 M HCl (2 mL), stirred for 10 min and evaporated. The process was repeated twice in order to exchange the TFA salt for an HCl salt. The prepared (S)-2-amino-6-((pent-4-enyloxy)carbonylamino)hexanoic acid HCl salt was dried under vacuum and then dissolved in DMAc:$H_2O$ (3 mL: 0.5 mL) containing $PdCl_2$ (8 mg, 0.045 mmol). The atmosphere of the flask was evacuated and replaced with $O_2$ three times. The reaction was then kept under $O_2$ atmosphere and heated to 80° C. for 8 h. The reaction was subsequently cooled to r.t., filtered, diluted with MeOH (5 mL) and precipitated into $Et_2O$. The filtrand was collected, giving 3 in 92% yield (259 mg, 0.83 mmol). $^1$H NMR ($D_2O$) δ=1.42-2.07 (m, 8H), 2.71 (s, 3H), 3.08-3.19 (m, 3H), 3.25 (m, 2H), 4.02 (m, 2H).

The aliphatic ketone bearing moiety is incorporated into polypeptide according to the present invention.

In this example, suitably a mutated/evolved tRNA synthetase is used to charge the tRNA with the aliphatic ketone bearing moiety. Suitably the tRNA synthetase comprises the amino acid sequence of SEQ ID NO:4, SEQ ID NO:6, SEQ ID NO:8, SEQ ID NO:10 or SEQ ID NO:12.

Example 3: Supplementary Methods

Chemical Synthesis

(S)-2-(tert-butoxycarbonylamino)-6-pent-4-ynamidohexanoic acid (8)

Boc-Lys-OH (1.0 g, 4.06 mmol) was dissolved in sat. aqueous NaHCO$_3$ (10 mL), THF (10 mL) was added, the solution was cooled to 0° C., and N-succinimidyl-4-pentynoate (594 mg, 3.04 mmol) was added. The reaction mixture was allowed to stir for 10 h at room temperature. The THF was evaporated in vacuo, and the aqueous solution was cooled to 0° C. and acidified with ice-cold 1 M HCl (100 mL). The aqueous layer was extracted with ice-cold EtOAc (2×100 mL), and the combined organic layers were dried over Na$_2$SO$_4$, filtered and concentrated in vacuo. The residue was further purified by silica gel chromatography using DCM:MeOH (9:1) as the eluent. The amide 7 was obtained in 70% yield (695 mg, 2.1 mmol) as a white foam. $^1$H NMR (CDCl$_3$): δ=1.31-1.82 (m, 15H), 2.01 (s, 1H), 2.36-2.50 (m, 4H), 3.20 (m, 2H), 4.13 (m, 1H), 5.55-5.75 (m, 2H), 6.73 (m, 1H). HRMS: m/z calcd for C$_{16}$H$_{26}$N$_2$O$_5$ [M+Na]: 349.1734. found: 349.1738.

(S)-2-amino-6-pent-4-ynamidohexanoic acid TFA salt (1)

To a solution of the amide 8 (600 mg, 1.8 mmol) in dry DCM (6 mL) was added TFA (6 mL), and the reaction mixture was allowed to stir for 1 h at room temperature. The solvents were evaporated under reduced pressure and the residue was precipitated through the addition of Et$_2$O, filtered and dried in vacuo, affording the clean amino acid 1 as a white solid in 95% yield (562 mg, 1.74 mmol). NMR (D$_2$O): 5=1.20-1.48 (m, 4H), 1.70-1.88 (m, 2H), 2.22-2.38 (m, 5H), 3.08 (m, 2H), 3.56 (m, 1H). HRMS: m/z calcd for C$_{11}$H$_{18}$N$_2$O$_3$ [M+H]$^+$: 227.1390. found: 227.1359.

(S)-2-(tert-butoxycarbonylamino)-6-((prop-2-ynyloxy)carbonylamino)hexanoic acid (9)

Boc-Lys-OH (500 mg, 2.03 mmol) was dissolved in 1 M NaOH (5 mL) and THF (5 mL) and cooled to 0° C. Propargyl chloroformate (158.4 mL, 192.5 mg, 1.62 mmol) was added dropwise over 5 minutes and the reaction was allowed to stir for 10 hours at room temperature. The solution was then cooled to 0° C. again, washed with ice-cold Et$_2$O (50 mL), acidified with ice-cold 1 M HCl (50 mL), and was extracted with ice-cold EtOAc (2×30 mL). The combined organic layers were dried over Na$_2$SO$_4$ and the solvents were evaporated to clean give 9 (442 mg, 1.35 mmol) as a white foam in 83% yield. $^1$H NMR (CDCl$_3$): δ=1.33-1.80 (m, 14H), 2.45 (s, 1H), 3.15 (m, 2H), 4.23 (m, 1H), 4.62-4.68 (m, 2H), 5.25-5.55 (m, 2H), 6.20-6.47 (m, 1H), 11.03 (s, 1H). $^{13}$C NMR (CDCl$_3$): δ=22.5, 28.5, 29.3, 32.1, 40.8, 52.6, 53.2, 74.8, 78.5, 80.3, 156.0, 157.3, 176.7. HRMS: m/z calcd for C$_{15}$H$_{24}$N$_2$O$_6$ [M+Na]$^+$: 351.15266. found: 351.15245.

(S)-2-amino-6-((prop-2-ynyloxy)carbonylamino)hexanoic acid TFA salt (2)

The propargyl carbamate 9 (400 mg, 1.22 mmol) was dissolved in dry DCM (4 mL). TFA (4 mL) was added dropwise and the reaction was allowed to stir for 1 h. The solvents were evaporated and the product was precipitated through the addition of ethyl ether, filtered and dried, affording clean 2 as a white solid in 96% yield (380 mg, 1.17 mmol). $^1$H NMR (D$_2$O): δ=1.25-1.45 (m, 4H), 1.76-1.88 (m, 2H), 2.75 (m, 1H), 3.02 (m, 2H), 3.93 (m, 1H), 4.53 (m, 2H). $^{13}$C NMR (D$_2$O): δ=21.3, 28.2, 29.2, 39.9, 52.5, 53.2, 75.4, 78.4, 117.8 (TFA), 157.5, 161.8 (TFA), 171.8. HRMS: m/z calcd for C$_{10}$H$_{16}$N$_2$O$_4$ [M+H]$^+$: 229.11828. found: 229.10841.

(S)-15-azido-2,2-dimethyl-4,12-dioxo-3,13-dioxa-5,11-diazapentadecane-6-carboxylic acid (10)

2-azidoethanol (500 mg, 5.74 mmol) was added to a solution of triphosgene (1.70 g, 5.74 mmol) in THF (10 mL) at 0° C. The reaction was stirred for 8 h, and the solvent was evaporated under vacuum. The residue was dried under vacuum for 1 h, affording 2-azidoethylchlroformate in 100% conversion as a clear oil. The chloroformate was dissolved in THF (1.5 mL) and slowly, added to a solution of Boc-Lys-OH (1.7 g, 6.88 mmol) in an aq. 1 M NaOH (20 mL)/THF (5 mL) solution at 0° C. The reaction mixture was stirred for 12 h and slowly warmed to room temperature. The solution was subsequently cooled to 0° C. and acidified to pH 2-3 with ice-cold aq. 1 M HCl solution. The aqueous layer was extracted with EtOAc (100 mL) and the organic layer was subsequently washed with brine (2×100 mL). The organic layer was then dried over Na$_2$SO$_4$, filtered, and evaporated, affording clean 10 in 80% yield (1.65 g, 4.59 mmol) without further purification. $^1$H NMR (acetone-d$_6$): δ=1.40-1.82 (m, 15H), 3.16 (m, 2H), 4.11 (m, 2H), 5.83-6.43 (m, 3H). $^{13}$C NMR (acetone-d$_6$): δ=23.0, 27.9, 31.6, 39.7, 50.4, 53.7, 63.0, 78.5, 156.0, 159.4, 174.2, 197.4.

(S)-2-amino-6-((2-azidoethoxy)carbonylamino)hexanoic acid TFA salt (3)

Compound 10 (1.5 g, 4.17 mmol) was dissolved in CH$_2$Cl$_2$ (15 mL) and TFA (15 mL) was slowly added to the solution. The reaction was stirred at room temperature for 30 min, after which the solvents were evaporated under vacuum. The residue was re-dissolved in MeOH (5 mL) and precipitated into Et$_2$O. The precipitate was collected and dried under vacuum, affording pure 3 in 93% yield (1.38 g, 3.87 mmol). NMR (D$_2$O): δ=1.22-1.45 (m, 4H), 1.67-1.73 (m, 2H), 2.99 (m, 2H), 3.38 (m, 2H), 3.70 (m, 1H), 4.09 (m, 2H). $^{13}$C NMR (D$_2$O): δ=21.4, 28.4, 29.6, 39.5, 53.4, 56.2, 57.8, 116.0 (TFA), 153.1, 162.3 (TFA), 172.9.

Expression and Purification of Myoglobin

To express sperm whale myoglobin with an incorporated unnatural amino acid, we transformed E. coli DH10B cells with pBKPylS and pMyo4TAGPylT-his6. Cells were recovered in 1 mL of LB media for 1 h at 37° C., before incubation (16 h, 37° C., 250 r.p.m.) in 100 mL of LB containing kanamycin (50 µg/mL) and tetracycline (25 µg/mL). 20 mL of this overnight culture was used to inoculate 500 mL of LB supplemented with kanamycin (25 µg/mL), tetracycline (12 µg/mL) and 2 mM of 2. Cells were grown (37° C., 250 r.p.m.), and protein expression was induced at OD$_{600}$-0.6, by addition of arabinose to a final concentration of 0.2%. After 3 h of induction, cells were harvested. Proteins were extracted by sonication at 4° C. The extract was clarified by centrifugation (20 min, 21,000 g, 4° C.), 300 µL of Ni$^{2+}$-NTA beads (Qiagen) were added to the extract, the mixture was incubated with agitation for 1 h at 4° C. Beads were collected by centrifugation (10 min, 1000 g). The beads were twice resuspended in 50 mL wash buffer and spun down at 1000 g. Subsequently, the beads were resuspended in 20 ml of wash buffer and transferred to a column. Protein was eluted in 1 ml of wash buffer supplemented with 200 mM imidazole and was then re-buffered to 20 mM ammonium bicarbonate using a sephadex G25 column. The purified proteins were analysed by 4-12% SDS-PAGE.

Expression of Myoglobin at Different Amino Acid Concentrations

*E. coli* DH10B cells containing pBKPylS and pMyo4TAGPylT were inoculated into LB containing kanamycin (50 µg/mL) and tetracycline (25 µg/mL). The cells were incubated with shaking overnight at 37° C. 200 µL of cells were inoculated into each of 3 mL LB aliquots containing kanamycin (25 µg/mL) and tetracycline (12 µg/mL) and supplemented with different concentrations (7.5 mM, 5 mM, 2.5 mM, 1 mM, 0.75 mM, 0.5 mM, 0.25 mM, 0.1 mM, 0 mM) of 2. After 3 h of incubation with shaking at 37° C., protein expression was induced by the addition of 30 µL of 20% arabinose. After 12 h of expression, cell were collected by centrifugation (16000 g, 5 min) of 1 mL of cell suspension. The cells were resuspended in 100 µL of NuPAGE SDS Sample buffer supplemented with 10% f3-mercaptoethanol, heated at 80° C. for 10 min and centrifuged at 16000 g for 10 min. The crude cell lysate was analysed by 4-12% SDS-PAGE. Western blots were performed with antibodies against the hexahistidine tag (Invitrogen AntiHis monoclonal Mouse antibody).

Protein Mass Spectrometry

Protein total mass was determined on an LCT time-of-flight mass spectrometer with electrospray ionization (ESI, Micromass). Proteins were rebuffered in 20 mM of ammonium bicarbonate and mixed 1:1 with formic acid (1% in methanol/$H_2O$=1:1). Samples were injected at 10 ml $min^{-1}$ and calibration was performed in positive ion mode using horse heart myoglobin. 60 scans were averaged and molecular masses obtained by deconvoluting multiply charged protein mass spectra using MassLynx version 4.1 (Micromass). Theoretical masses of wild-type proteins were calculated using Protparam (http://us.expasy.org/tools/protparam.html), and theoretical masses for unnatural amino acid containing proteins were adjusted manually.

Bioconjugation Via Copper-Catalysed [3+2]-Cycloaddition Reactions

Protein was re-buffered to 100 mM sodium phosphate buffer (pH 8.3) and concentrated to 2.5 mg/mL. 100 mM stock solutions of $CuSO_4$, sulfonated bathophenanthroline sodium salt (GFS Chemicals) and sodium ascorbate in water were prepared, pre-mixed and incubated at room temperature for 5 min. Myoglobin containing 2 (13.5 nmol) was reacted for 15 minutes at 25° C., then 4° C. for 18 h with the biotin azide (Quanta Biodesign) 5 or the By3 azide (Primetech LTD) 6 (50 equivalents, 10 mM in DMSO) and $CuSO_4$ (1 mM)/ascorbate (1 mM)/ligand (2 mM)[20]. After 18 h, the solutions were diluted to 1 mL and loaded onto an Illustra™ NAP-10 column. Proteins were eluted into 1.5 mL of 20 mM $NH_4HCO_3$, dialyzed overnight with 20 mM $NH_4HCO_3$, loaded onto PD10 and eluted into 3.5 mL 20 mM $NH_4HCO_3$. The solution was concentrated to 200 mL using Amicon Ultra® Centrifugal Filter Devices (10,000 kDa, Millipore). Protein concentration of the labeled samples were measured by BCA Protein Assay (Thermo Scientific). The Biotin Quantitation Kit (Thermo Scientific) was used to quantify biotin-conjugated protein in labeled samples, and the By3 absorbance at 550 nm was used to quantify purified By3-labeled protein. The molar ratio of the label (By3 or biotin) to protein defines the labeling efficiency.

Example 4

Figure 6:
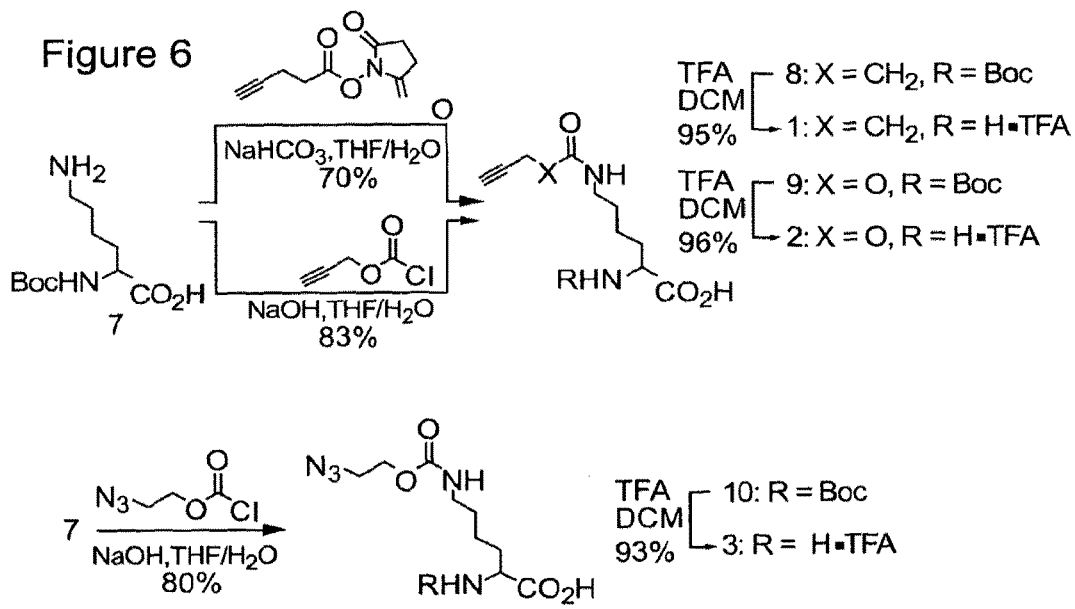
FIG. 6 shows Supplementary Scheme 1. Synthesis of the amide-linked alkyne 1, the carbamate-linked alkyne 2, and the carbamate-linked azide 3.

Reference is made to FIG. 6

Amino acids were synthesized that link the alkyne functionality to the side-chain amine of lysine through either an amide (1) or a carbamate (2) linkage (FIG. 6—Supplementary Scheme 1). The synthesis of these amino acids commences with the Boc-protected lysine 7 (Chem-Impex International, Inc), which was reacted with N-succinimidyl-4-pentynoate (prepared by a DCC mediated coupling of 4-pentynoic acid with N-hydroxysuccinimide (Slater, M.; Snauko, M.; Svec, F.; Frechet, J. M. *J. Anal. Chem.* 2006, 78, 4969-4975)) in the presence of $NaHCO_3$ furnishing 8 in 70% yield. The amide 7 was then deprotected with TFA in $CH_2Cl_2$ delivering the amino acid 1 in 95% yield. In order to synthesize 2, the protected lysine 7 was reacted with prop-2-ynyl chloroformate in presence of aqueous NaOH. The carbamate 9 was obtained in 83% yield, and subsequently deprotected with TFA in $CH_2Cl_2$, delivering the amino acid 2 in 96% yield. A similar sequence was conducted by reacting 7 with 3-azidoethyl chloroformate in aqueous NaOH, delivering 10 in 80% yield. The amino acid 3 was obtained through a deprotection with TFA in 93%.

Figure 7A:
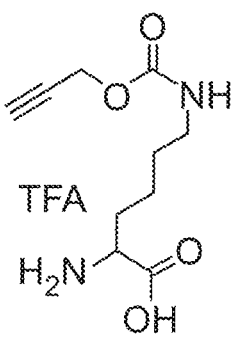
FIG. 7 shows Supplementary FIG. 1 A-E: NMR spectra of compounds 1, 2 and 3.
Figure 7A:
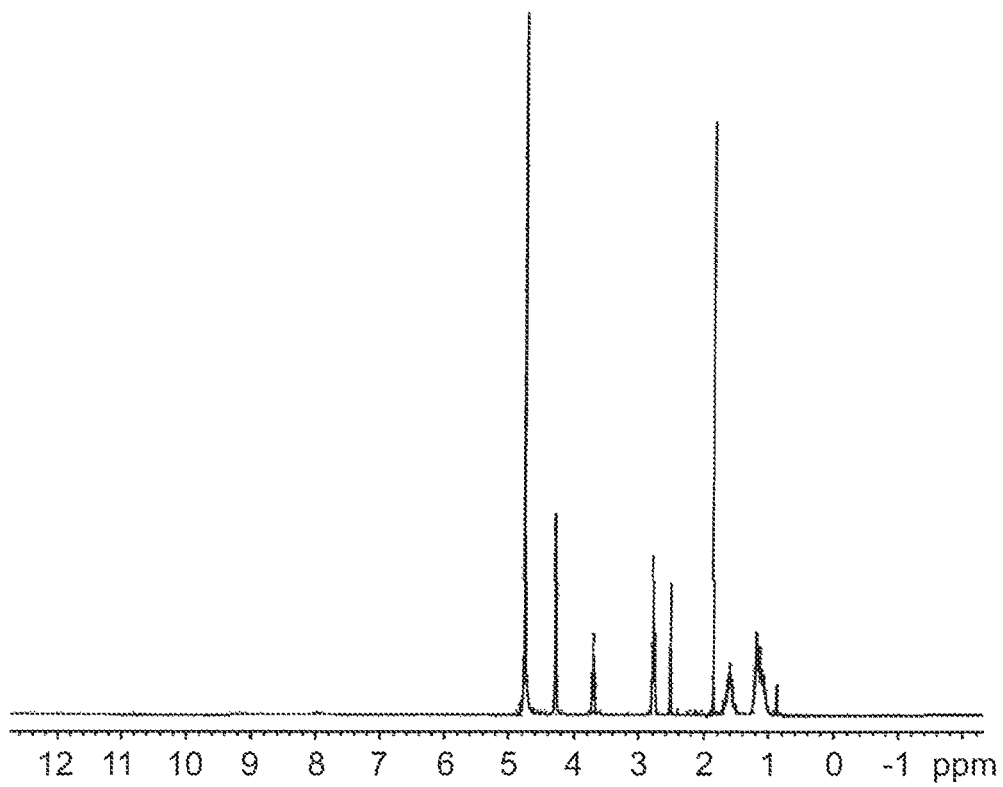

Spectra are shown in FIG. 7 A-E.

Example 5

Figure 2:
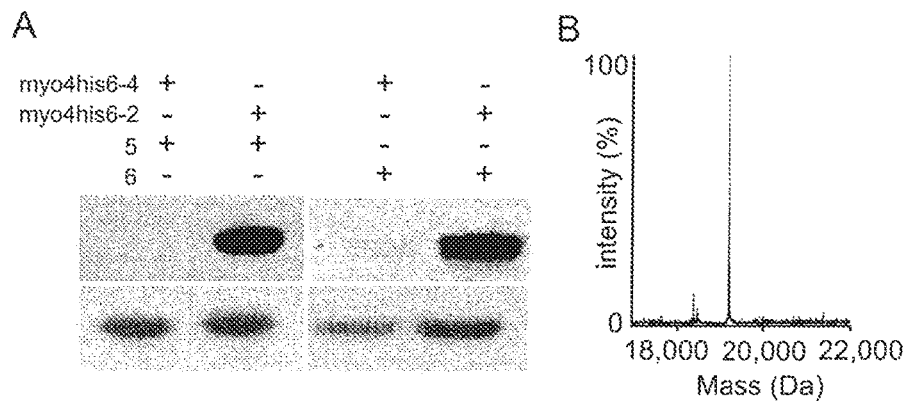
FIG. 2 shows: A. Efficient and specific labeling of genetically encoded 2 with azido-probes. Left. The biotin azide 5 labeling reaction was performed on myoglobin containing 4 or 2 at position 4 (myo-4-his6-4 and myo-4-his6-2). Proteins were probed for biotin (top). Right. By3 labeling with 6 was imaged directly. Coomassie stained protein gels (bottom) demonstrate equal protein recovery in the samples. B. ESI-MS of the myoglobin-his6 containing 2 labeled with biotin azide 5 (Found: 19199.5±1.5 Da, expected: 19198.2 Da)
Figure 8:
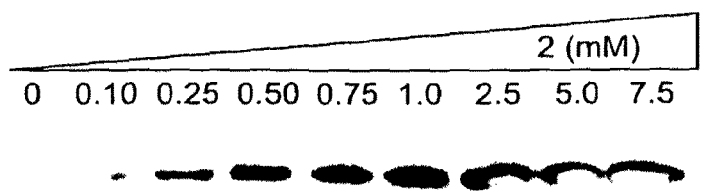
FIG. 8 shows Supplementary
Figure 8:
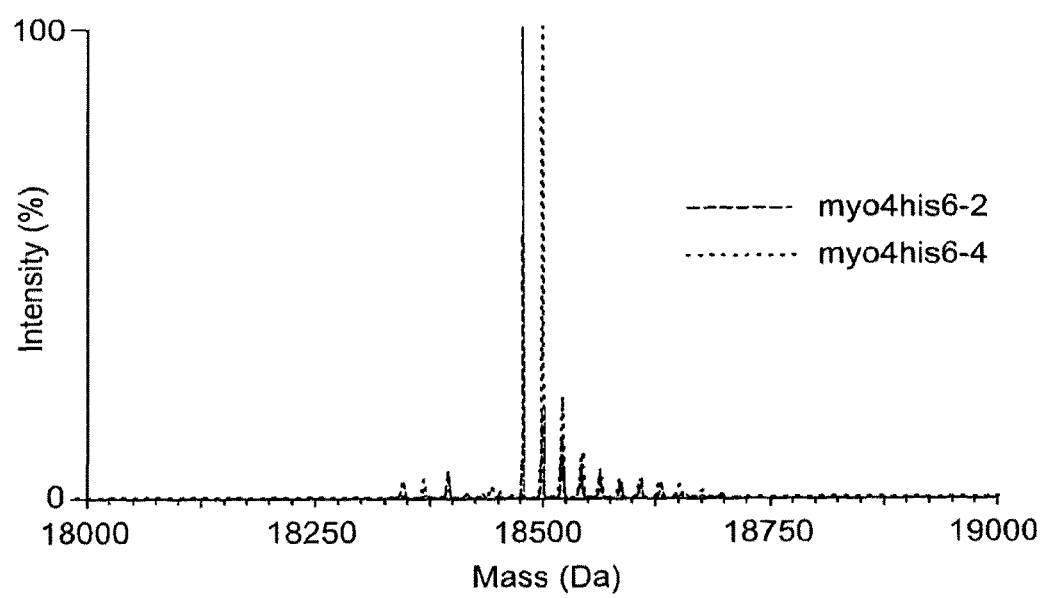
Figure 8:
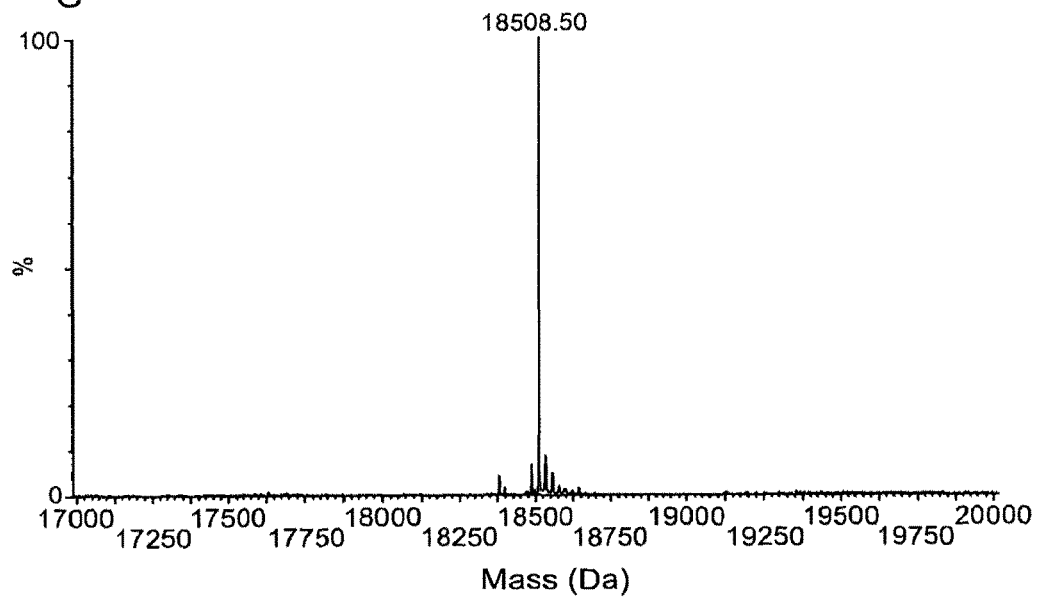

Reference is made to FIG. 8 (Supplementary FIG. 2).

A. The increase in full length protein synthesis as a function of amino acid concentration. Western blots against his-6 show the increase in myoglobin-his6 incorporating 2 in cell-lysates B. Electrospray ionization mass spectra of myoglobin-his6 incorporating 2 (orange) or 4 (blue). Myoglobin-his6 incorporating 2 has an expected mass of 18478.2 Da and a found mass of 18477.4. Myoglobin-his6 incorporating 4 has an expected mass of 18496.0 Da and a found mass of 18496.2 Da. C. Electrospray ionization mass spectra of myoglobin-his6 incorporating the azide (3). Found mass 18508.5+/−1 Da, expected mass 18509.2 Da)

Figure 3:
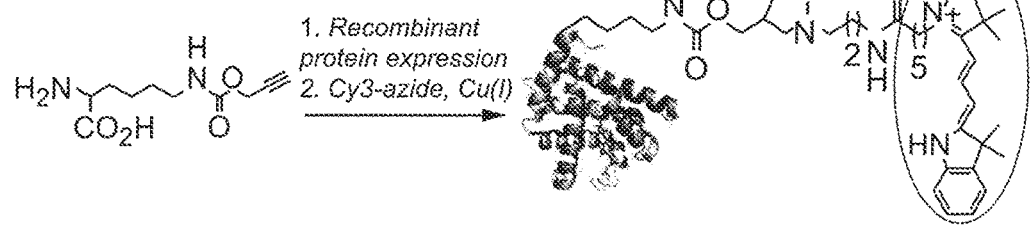
FIG. 3 shows formulae and a reaction diagram
Figure 4:
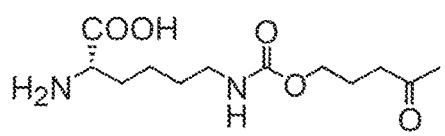
FIG. 4 shows aliphatic ketone
Figure 9:
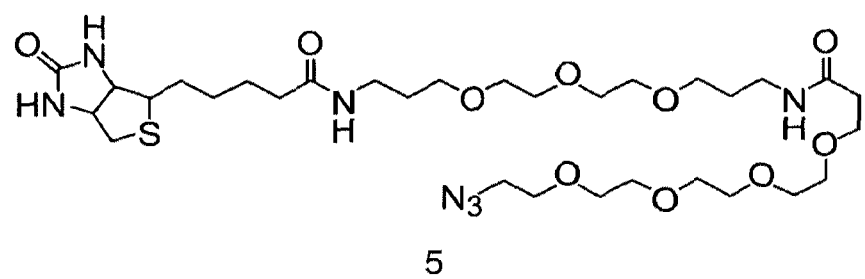
FIG. 9 shows Supplementary
Figure 9:
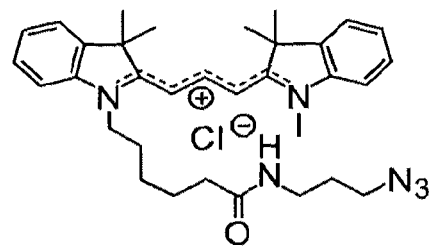

FIG. 9 shows Supplementary FIG. 3: The structures of the biotin azide 5 and By3 azide 6 used.

REFERENCES

1. Hermanson, G. T., Bioconjugate Techniques. Academic Press: 1996.
2. Kiick, K. L.; Saxon, E.; Tirrell, D. A.; Bertozzi, C. R., PNAS USA 2002, 99, 19-24.
3. Datta, D.; Wang, P.; Carrico, I. S.; Mayo, S. L.; Tirrell, D. A., J Am Chem Soc 2002, 124, 5652-3.
4. Xie, J.; Schultz, P. G., Nat Rev Mol Cell Biol 2006, 7, 775-82.
5. Chin, J. W.; Santoro, S. W.; Martin, A. B.; King, D. S.; Wang, L.; Schultz, P. G., J Am Chem Soc 2002, 124, 9026-7.
6. Chin, J. W.; Cropp, T. A.; Anderson, J. C.; Mukherji, M.; Zhang, Z.; Schultz, P. G., Science 2003, 301, 964-7.
7. Deiters, A.; Schultz, P. G., Bioorg Med Chem Lett 2005, 15, 1521-4.
8. Zhang, Z.; Smith, B. A.; Wang L.; Brock, A.; Cho, C.; Schultz, P. G., Biochemistry 2003, 42, 6735-46.
9. Ambrogelly, A.; Gundllapalli, S.; Herring, S.; Polycarpo, C.; Frauer, C.; Soll, D., Proc Natl Acad Sci USA 2007, 104, 3141-6.
10. Neumann, H.; Peak-Chew, S. Y.; Chin, J. W., Nat Chem Biol 2008, 4, 232-4.

11. Yanagisawa, T.; Ishii, R.; Fukunaga, R.; Kobayashi, T.; Sakamoto, K.; Yokoyama, S., Chem Biol 2008, 15, 1187-97.
12. Mukai, T.; Kobayashi, T.; Hino, N.; Yanagisawa, T.; Sakamoto, K.; Yokoyama, S., Biochem Biophys Res Commun 2008, 371, 818-22.
13. Kolb, H. C.; Finn, M. G.; Sharpless, K. B., Angew Chem Int Ed Engl. 2001, 40, 2004-2021.
14. Fekner, T.; Li, X.; Lee, M. M.; Chan, M. K., Angewandte Chemie 2009, 121, 1661-1663.
15. Schoffelen, S.; Lambermon, M. H.; van Eldijk, M. B.; van Hest, J. C., Bioconjug Chem 2008, 19, 1127-31.
16. Kozlowski, A.; Harris, J. M., J Control Release 2001, 72, 217-24.
17. Wang, K.; Neumann, H.; Peak-Chew, S. Y.; Chin, J. W., Nat Biotechnol 2007, 25, 770-7.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

SEQUENCE LISTING

SEQ ID NO: 1

```
>MbPylS MS (Translated from Genbank accession number AY273828,
protein ID: AAQ19545.1)
MDKKPLDVLISATGLWMSRTGTLHKIKHHEVSRSKIYIEMACGDHLVVNNSRSCRTARAF
RHHKYRKTCKRCRVSDEDINNFLTRSTESKNSVKVRVVSAPKVKKAMPKSVSRAPKPLEN
SVSAKASTNTSRSVPSPAKSTPNSSVPASAPAPSLTRSQLDRVEALLSPEDKISLNMAKP
FRELEPELVTRRKNDFQRLYTNDREDYLGKLERDITKFFVDRGFLEIKSPILIPAEYVER
MGINNDTELSKQIFRVDKNLCLRPMLAPTLYNYLRKLDRILPGPIKIFEVGPCYRKESDG
KEHLEEFTMVNFCQMGSGCTRENLEALIKEFLDYLEIDFEIVGDSCMVYGDTLDIMHGDL
ELSSAVVGPVSLDREWGIDKPWIGAGFGLERLLKVMHGFKNIKRASRSESYYNGISTNL
```

SEQ ID NO: 2

```
MbPylS (strain MS), codon optimized
atggataaaaaaccgctggatgtgctgattagcgcgaccggcctgtggat
gagccgtaccggcaccctgcataaaatcaaacatcatgaagtgagccgca
gcaaaatctatattgaaatggcgtgcggcgatcatctggtggtgaacaac
agccgtagctgccgtaccgcgcgtgcgtttcgtcatcataaataccgcaa
aacctgcaaacgttgccgtgtgagcgatgaagatatcaacaactttctga
cccgtagcaccgaaagcaaaaacagcgtgaaagtgcgtgtggtgagcgcg
ccgaaagtgaaaaaagcgatgccgaaaagcgtgagccgtgcgccgaaacc
gctggaaatagcgtgagcgcgaaagcgagcaccaacaccagccgtagcg
ttccgagcccggcgaaaagcacccccgaacagcagcgttccggcgtctgcg
ccggcaccgagcctgacccgcagccagctggatcgtgtggaagcgctgct
gtctccggaagataaaattagcctgaacatggcgaaaccgtttcgtgaac
tggaaccggaactggtgacccgtcgtaaaaacgattttcagcgcctgtat
accaacgatcgtgaagattatctgggcaaactggaacgtgatatccaccaa
attttttgtggatcgcggcttctggaaattaaaagcccgattctgattc
cggccggaatatgtggaacgtATGggcattaacaacgacaccgaactgagc
aaacaaattttccgcgtggataaaaaacctgtgcctgcgtccgatgctgGC
CccgaccctgTATaactatCTGcgtaaactggatcgtattctgccgggtc
cgatcaaaattttgaagtgggcccgtgctatcgcaaagaaagcgatggc
aaagaacacctggaagaattcaccatggttaacttttTGCcaaatgggcag
cggctgcacccgtgaaaacctggaagcgctgatcaaagaattcctggatt
atctggaaatcgacttcgaaattgtgggcgatagctgcatggtgtatggc
gataccctggatattatgcatggcgatctggaactgagcagcgcggtggt
gggtccggttagcctggatcgtgaatggggcattgataaaccgtggattg
gcgcgggttttggcctggaacgtctgctgaaagtgatgcatggcttcaaa
aacattaaacgtgcgagccgtagcgaaagctactataacggcattagcac
gaacctgtaa
```

SEQ ID NO: 3

```
tRNAcua
MbPylT (strain MS, from Genbank accession number AY064401)
gggaacctgatcatgtagatcgaatggactctaaatccgttcagccgggt
tagattcccggggtttccgcca
```

SEQ ID NO: 4

```
>KtKRS-1
MDKKPLDVLISATGLWMSRTGTLHKIKHHEVSRSKIYIEMACGDHLVVNNSRSCRTARAF
RHHKYRKTCKRCRVSDEDINNFLTRSTESKNSVKVRVVSAPKVKKAMPKSVSRAPKPLEN
SVSAKASTNTSRSVPSPAKSTPNSSVPASAPAPSLTRSQLDRVEALLSPEDKISLNMAKP
FRELEPELVTRRKNDFQRLYTNDREDYLGKLERDITKFFVDRGFLEIKSPILIPAEYVER
MGINNDTELSKQIFRVDKNLCLRPMLAPTLYNYQRKLDRILPGPIKIFEVGPCYRKESDG
KEHLEEFTMVNFCQMGSGCTRENLEALIKEFLDYLEIDFEIVGDSCMVYGDTLDIMHGDL
ELSSAVVGPVSLDREWGIDKPWIGAGFGLERLLKVMHGFKNIKRASRSESYYNGISTNL
Mutations in KtKRS-1: L274Q
```

SEQ ID NO: 5

```
KtKRS-1 (mutations relative to MbPylS MS in upper case)
atggataaaaaaccgctggatgtgctgattagcgcgaccggcctgtggat
gagccgtaccggcaccctgcataaaatcaaacatcatgaagtgagccgca
```

```
                              SEQUENCE LISTING
gcaaaatctatattgaaatggcgtgcggcgatcatctggtggtgaacaac
agccgtagctgccgtaccgcgcgtgcgtttcgtcatcataaataccgcaa
aacctgcaaacgttgccgtgtgagcgatgaagatatcaacaactttctga
cccgtagccaccgaaagcaaaaacagcgtgaaagtgcgtgtggtgagcgcg
ccgaaagtgaaaaaagcgatgccgaaaagcgtgagccgtgcgccgaaacc
gctggaaaatagcgtgagcgcgaaagcgagccaacaccagccgtagcg
ttccgagcccggcgaaaagcaccccgaacagcagcgttccggcgtctgcg
ccggcaccgagcctgacccgcagccagctggatcgtgtggaagcgctgct
gtctccggaagataaaattagcctgaacatggcgaaaccgtttcgtgaac
tggaaccggaactggtgacccgtcgtaaaaacgattttcagcgcctgtat
accaacgatcgtgaagattatctgggcaaactggaacgtgatatcaccaa
attttttgtggatcgcggctttctggaaattaaaagcccgattctgattc
cggcggaatatgtggaacgtatgggcattaacaacgacaccgaactgagc
aaacaaattttccgcgtggataaaaacctgtgcctgcgtccgatgctggc
GccgaccctgtataactatcAgcgtaaactggatcgtattctgccgggtc
cgatcaaattttttgaagtgggcccgtgctatcgcaaagaaagcgatggc
aaagaacacctggaagaattcaccatggttaactttTgTcaaatgggcag
cggctgcacccgtgaaaacctggaagcgctgatcaaagaattcctggatt
atctggaaatcgacttcgaaattgtgggcgatagctgcatggtgtatggc
gataccctggatattatgcatggcgatctggaactgagcagcgcggtggt
gggtccggttagcctggatcgtgaatggggcattgataaaccgtggattg
gcgcgggttttggcctggaacgtctgctgaaagtgatgcatggcttcaaa
aacattaaacgtgcgagccgtagcgaaagctactataacggcattagcac
gaacctgtaa
                                                       SEQ ID NO: 6
>KtKRS-2
MDKKPLDVLISATGLWMSRTGTLHKIKHHEVSRSKIYIEMACGDHLVVNNSRSCRTARAF
RHHKYRKTCKRCRVSDEDINNFLTRSTESKNSVKVRVVSAPKVKKAMPKSVSRAPKPLEN
SVSAKASTNTSRSVPSPAKSTPNSSVPASAPAPSLTRSQLDRVEALLSPEDKISLNMAKP
FRELEPELVTRRKNDFQRLYTNDREDYLGKLERDITKFFVDRGFLEIKSPILIPAEYVER
MGINNDTELSKQIFRVDKNLCLRPMLAPTLYNYNRKLDRILPGPIKIFEVGPCYRKESDG
KEHLEEFTMVNFVQMGSGCTRENLEALIKEFLDYLEIDFEIVGDSCMVYGDTLDIMHGDL
ELSSAVVGPVSLDREWGIDKPWIGAGFGLERLLKVMHGFKNIKRASRSESYYNGISTNL
Mutations in KtKRS-2: L274N, C313V
                                                       SEQ ID NO: 7
KtKRS-2 (mutations relative to MbPylS MS in upper case)
atggataaaaaaccgctggatgtgctgattagcgcgaccggcctgtggat
gagccgtaccggcacccctgcataaaatcaaacatcatgaagtgagccgca
gcaaaatctatattgaaatggcgtgcggcgatcatctggtggtgaacaac
agccgtagctgccgtaccgcgcgtgcgtttcgtcatcataaataccgcaa
aacctgcaaacgttgccgtgtgagcgatgaagatatcaacaactttctga
cccgtagccaccgaaagcaaaaacagcgtgaaagtgcgtgtggtgagcgcg
ccgaaagtgaaaaaagcgatgccgaaaagcgtgagccgtgcgccgaaacc
gctggaaaatagcgtgagcgcgaaagcgagccaacaccagccgtagcg
ttccgagcccggcgaaaagcaccccgaacagcagcgttccggcgtctgcg
ccggcaccgagcctgacccgcagccagctggatcgtgtggaagcgctgct
gtctccggaagataaaattagcctgaacatggcgaaaccgtttcgtgaac
tggaaccggaactggtgacccgtcgtaaaaacgattttcagcgcctgtat
accaacgatcgtgaagattatctgggcaaactggaacgtgatatcaccaa
attttttgtggatcgcggctttctggaaattaaaagcccgattctgattc
cggcggaatstgtggaacgtatgggcattaacaacgacaccgaactgagc
aaacaaattttccgcgtggataaaaacctgtgcctgcgtccgatgctggc
GccgaccctgtataactatAATcgtaaactggatcgtattctgccgggtc
cgatcaaattttttgaGgtgggcccgtgctatcgcaaagaaagcgatggc
aaagaacacctggaagaattcaccatggttaactttGTGcaaatgggcag
cggctgcacccgtgaaaacctggaagcgctgatcaaagaattcctggatt
atctggaaatcgacttcgaaattgtgggcgatagctgcatggtgtatggc
gataccctggatattatgcatggcgatctggaactgagcagcgcggtggt
gggtccggttagcctggatcgtgaatggggcattgataaaccgtggattg
gcgcgggttttggcctggaacgtctgctgaaagtgatgcatggcttcaaa
aacattaaacgtgcgagccgtagcgaaagctactataacggcattagcac
gaacctgtaa
                                                       SEQ ID NO: 8
>KtKRS-3
MDKKPLDVLISATGLWMSRTGTLHKIKHHEVSRSKIYIEMACGDHLVVNNSRSCRTARAF
RHHKYRKTCKRCRVSDEDINNFLTRSTESKNSVKVRVVSAPKVKKAMPKSVSRAPKPLEN
SVSAKASTNTSRSVPSPAKSTPNSSVPASAPAPSLTRSQLDRVEALLSPEDKISLNMAKP
FRELEPELVTRRKNDFQRLYTNDREDYLGKLERDITKFFVDRGFLEIKSPILIPAEYVER
MGINNDTELSKQIFRVDKNLCLRPMLAPTLYNYNRKLDRILPGPIKIFEVGPCYRKESDG
KEHLEEFTMVNFVQMGSGCTRENLEALIKEFLDYLEIDFEIVGDSCMVYGDTLDIMHGDL
ELSSAVVGPVSLDREWGIDKPWIGAGFGLERLLKVMHGFKNIKRASRSESYYNGISTNL
Peptide sequence corresponds to KtKRS-2: Mutations in KtKRS-2:
L274N, C313V: nucleotide sequence differs from KtKRS-2.
```

SEQUENCE LISTING

SEQ ID NO: 9
KtKRS-3 (mutations relative to MbPylS MS in upper case)
```
atggataaaaaaccgctggatgtgctgattagcgcgaccggcctgtggat
gagccgtaccggcaccctgcataaaatcaaacatcatgaagtgagccgca
gcaaaatctatattgaaatggcgtgcggcgatcatctggtggtgaacaac
agccgtagctgccgtaccgcgcgtgcgtttcgtcatcataaataccgcaa
aacctgcaaacgttgccgtgtgagcgatgaagatatcaacaactttctga
cccgtagcaccgaaagcaaaaacagcgtgaaagtgcgtgtggtgagcgcg
ccgaaagtgaaaaaagcgatgccgaaaagcgtgagccgtgcgccgaaacc
gctggaaatagcgtgagcgcgaaagcgagcaccaacaccagccgtagcg
ttccgagcccggcgaaaagcaccccgaacagcagcgttccggcgtctgcg
ccggcaccgagcctgacccgcagcagctggatcgtgtggaagcgctgct
gtctccggaagataaaattagcctgaacatggcgaaaccgtttcgtgaac
tggaaccggaactggtgacccgtcgtaaaaacgattttcagcgcctgtat
accaacgatcgtgaagattatctgggcaaactggaacgtgatatcaccaa
attifttgtggatcgcggctttctggaaattaaaagcccgattctgattc
cggcggaatatgtggaacgtatgggcattaacaacgacaccgaactgagc
aaacaaattttccgcgtggataaaaacctgtgcctgcgtccgatgctggc
GccgaccctgtataactatAATcgtaaactggatcgtattctgccgggtc
cgatcaaaattttttgaagtgggcccgtgctatcgcaaagaaagcgatgc
aaagaacacctggaagaattcaccatggttaactttGTTcaaatgggcag
cggctgcacccgtgaaaacctggaagcgctgatcaaagaattcctggatt
atctggaaatcgacttcgaaattgtgggcgatagctgcatggtgtatggc
gatacccggatattatgcatggcgatctggaactgagcagcgcggtggt
gggtccggttagcctggatcgfgaatgggcattgataaaccgtggattg
gcgcgggttttggcctggaacgtctgctgaaagtgatgcatggcttcaaa
aacattaaacgtgcgagccgtagcgaaagctactataacggcattagcac
gaacctgtaa
```

SEQ ID NO: 10
>KtKRS-4
```
MDKKPLDVLISATGLWMSRTGTLHKIKHHEVSRSKIYIEMACGDHLVVNNSRSCRTARAF
RHHKYRKTCKRCRVSDEDINNFLTRSTESKNSVKVRVVSAPKVKKAMPKSVSRAPKPLEN
SVSAKASTNTSRSVPSPAKSTPNSSVPASAPAPSLTRSQLDRVEALLSPEDKISLNMAKP
FRELEPELVTRRKNDFQRLYTNDREDYLGKLERDITKFFVDRGFLEIKSPILIPAEYVER
MGINNDTELSKQIFRVDKNLCLRPMLAPTLYNYMRKLDRILPGPIKIFEVGPCYRKESDG
KEHLEEFTMVNFAQMGSGCTRENLEALIKEFLDYLEIDFEIVGDSCMVYGDTLDIMHGDL
ELSSAVVGPVSLDREWGIDKPWIGAGFGLERLLKVMHGFKNIKRASRSESYYNGISTNL
Mutations in KtKRS-4: L274M, C313A
```

SEQ ID NO: 11
KtKRS-4 (mutations relative to MbPyls MS in upper case)
```
atggataaaaaaccgctggatgtgctgattagcgcgaccggcctgtggat
gagccgtaccggcaccctgcataaaatcaaacatcatgaagtgagccgca
gcaaaatctatattgaaatggcgtgcggcgatcatctggtggtgaacaac
agccgtagctgccgtaccgcgcgtgcgtttcgtcatcataaataccgcaa
aacctgcaaacgttgccgtgtgagcgatgaagatatcaacaactttctga
cccgtagcaccgaaagcaaaaacagcgtgaaagtgcgtgtggtgagcgcg
ccgaaagtgaaaaaagcgatgccgaaaagcgtgagccgtgcgccgaaacc
gctggaaatagcgtgagcgcgaaagcgagcaccaacaccagccgtagcg
ttccgagcccggcgaaaagcaccccgaacagcagcgttccggcgtctgcg
ccggcaccgagcctgacccgcagcagctggatcgtgtggaagcgctgct
gtctccggaagataaaattagcctgaacatggcgaaaccgtttcgtgaac
tggaaccggaactggtgacccgtcgtaaaaacgattttcagcgcctgtat
accaacgatcgtgaagattatctgggcaaactggaacgtgatatcaccaa
attttttgtggatcgcggctttctggaaattaaaagcccgattctgattc
cggcggaatatgtggaacgtatgggcattaacaacgacaccgaactgagc
aaacaaattttccgcgtggataaaaacctgtgcctgcgtccgatgctggc
TccgaccctgtataactatAtgcgtaaactggatcgtattctgccgggtc
cgatcaaaattttttgaagtgggcccgtgctatcgcaaagaaagcgatgc
aaagaacacctggaagaattcaccatggttaactttGCTcaaatgggcag
cggctgcacccgtgaaaacctggaagcgctgatcaaagaattcctggatt
atctggaaatcgacttcgaaattgtgggcgatagctgcatggtgtatggc
gatacccggatattatgcatggcgatctggaactgagcagcgcggtggt
gggtccggttagcctggatcgtgaatgggcattgataaaccgtggattg
gcgcgggttttggcctggaacgtctgctgaaagtgatgcatggcttcaaa
aacattaaacgtgcgagccgtagcgaaagctactataacggcattagcac
gaacctgtaa
```

SEQ ID NO: 12
>KtKRS-5
```
MDKKPLDVLISATGLWMSRTGTLHKIKHHEVSRSKIYIEMACGDHLVVNNSRSCRTARAF
RHHKYRKTCKRCRVSDEDINNFLTRSTESKNSVKVRVVSAPKVKKAMPKSVSRAPKPLEN
SVSAKASTNTSRSVPSPAKSTPNSSVPASAPAPSLTRSQLDRVEALLSPEDKISLNMAKP
FRELEPELVTRRKNDFQRLYTNDREDYLGKLERDITKFFVDRGFLEIKSPILIPAEYVER
MGINNDTELSKQIFRVDKNLCLRPMLAPTLYNYTRKLDRILPGPIKIFEVGPCYRKESDG
```

KEHLEEFTMVNF<u>V</u>QMGSGCTRENLEALIKEFLDYLEIDFEIVGDSCMVYGDTLDIMHGDL
ELSSAVVGPVSLDREWGIDKPWIGAGFGLERLLKVMHGFKNIKRASRSESYYNGISTNL
Mutations in KtKRS-5: L274T, C313V

SEQ ID NO: 13

KtKRS-5 (mutations relative to MbPylS MS in upper case)
atggataaaaaaaccgctggatgtgctgattagcgcgaccggcctgtggat
gagccgtaccggcaccctgcataaaatcaaacatcatgaagtgagccgca
gcaaaatctatattgaaatggcgtgcggcgatcatctggtggtgaacaac
agccgtagctgccgtaccgcgcgtgcgtttcgtcatcataaataccgcaa
aacctgcaaacgttgccgtgtgagcgatgaagatatcaacaactttctga
cccgtagcaccgaaagcaaaaacagcgtgaaagtgcgtgtggtgagcgcg
ccgaaagtgaaaaaagcgatgccgaaaagcgtgagccgtgcgccgaaacc
gctggaaaatagcgtgagcgcgaaagcgagcaccaacaccagccgtagcg
ttccgagcccggcgaaaagcaccccgaacagcagcgttccggcgtctgcg
ccggcaccgagcctgacccgcagccagctggatcgtgtggaagcgctgct
gtctccggaagataaaattagcctgaacatggcgaaaccgtttcgtgaac
tggaaccggaactggtgacccgtcgtaaaaacgattttcagcgcctgtat
accaacgatcgtgaagattatctgggcaaactggaacgtgatatcaccaa
atttttttgtggatcgcggctttctggaaattaaaagcccgattctgattc
cggcggaatatgtggaacgtatgggcattaacaacgacaccgaactgagc
aaacaaattttccgcgtggataaaaacctgtgcctgcgtccgatgctggc
GccgaccctgtataactatACGcgtaaactggatcgtattctgccgggtc
cgatcaaaattttttgaagtgggcccgtgctatcgcaaagaaagcgatggc
aaagaacacctggaagaattcaccatggttaactttGTGcaaatgggcag
cggctgcacccgtgaaaacctggaagcgctgatcaaagaattcctggatt
atctggaaatcgacttcgaaattgtgggcgatagctgcatggtgtatggc
gataccctggatattatgcatggcgatctggaactgagcagcgcggtggt
gggtccggttagcctggatcgtgaatgggcattgataaaccgtggattg
gcgcgggttttggcctggaacgtctgctgaaagtgatgcatggcttcaaa
aacattaaacgtgcgagccgtagcgaaagctactataacggcattagcac
gaacctgtaa

---

The invention claimed is:

1. A method of making a polypeptide comprising an orthogonal functional group, said orthogonal functional group being comprised by an aliphatic amino acid comprising an alkyne group or an azide group, wherein said aliphatic amino acid does not comprise an aromatic moiety, said method comprising providing a host cell; providing a nucleic acid encoding the polypeptide of interest; providing a tRNA-tRNA synthetase pair orthogonal to said host cell; adding said amino acid comprising the orthogonal functional group of interest, wherein said amino acid is a substrate for said orthogonal tRNA synthetase and incubating to allow incorporation of said amino acid into the polypeptide of interest via the orthogonal tRNA-tRNA synthetase pair.

2. A method according to claim 1 wherein incorporation is mediated by an amber codon specified by said nucleic acid.

3. A method according to claim 1 wherein the amino acid is or is derived from lysine.

4. A method according to claim 1 wherein the orthogonal tRNA-tRNA synthetase pair are a cognate pair capable of acting on pyrrolysine.

5. A method according to claim 1 wherein the orthogonal tRNA-tRNA synthetase pair have sequences identical to the wild type sequences of the organism in which they naturally occur.

6. A method according to claim 4 wherein the tRNA-tRNA synthetase pair is MbtRNA$_{CUA}$ and MbPylRS.

7. A method according to claim 6 wherein the MbtRNA$_{CUA}$ comprises the nucleotide sequence of SEQ ID NO:3 and the MbPylRS comprises the amino acid sequence of SEQ ID NO:1.

8. A method according to claim 1 wherein the host cell is *E. coli*.

9. A method according to claim 1 wherein said tRNA synthetase is a tRNA synthetase having the amino acid sequence of SEQ ID NO:4, SEQ ID NO:6, SEQ ID NO:8, SEQ ID NO:10 or SEQ ID NO:12.

10. A method according to claim 1 wherein said tRNA synthetase is encoded by a nucleic acid comprising the nucleotide sequence of SEQ ID NO:5, SEQ ID NO:7, SEQ ID NO:9, SEQ ID NO:11 or SEQ ID NO:13.

11. A method according to claim 5 wherein the tRNA-tRNA synthetase pair is MbtRNA$_{CUA}$ and MbPylRS.

12. A method according to claim 11 wherein the MbtRNA$_{CUA}$ comprises the nucleotide sequence of SEQ ID NO:3 and the MbPylRS comprises the amino acid sequence of SEQ ID NO:1.

13. A method according to claim 1 wherein the functional group comprises an azide group.

14. A method of making a polypeptide comprising an orthogonal functional group, said orthogonal functional group being comprised by an aliphatic amino acid comprising an alkyne group or an azide group, wherein the aliphatic amino acid does not comprise an aromatic moiety, said method comprising providing a host cell; providing a nucleic acid encoding the polypeptide of interest; providing a tRNA-tRNA synthetase pair orthogonal to said host cell, wherein said orthogonal tRNA-tRNA synthetase pair have sequences identical to the wild type sequences of the organism in which they naturally occur; adding said amino acid comprising the orthogonal functional group of interest, wherein said amino acid is a substrate for said orthogonal tRNA synthetase and incubating to allow incorporation of said amino acid into the polypeptide of interest via the orthogonal tRNA-tRNA synthetase pair.

* * * * *